US008796202B2

(12) United States Patent
Chen et al.

(10) Patent No.: US 8,796,202 B2
(45) Date of Patent: Aug. 5, 2014

(54) MULTI-VALENT POLY-UBL CHAIN INHIBITORS AND METHODS OF USE

(75) Inventors: Yuan Chen, Arcadia, CA (US); David Horne, Duarte, CA (US); Yi-Jia Li, Duarte, CA (US); Yuelong Ma, Duarte, CA (US); Angela L. Perkins-Harki, Minneapolis, MN (US); Yang Su, Beijing (CN)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 13/401,642

(22) Filed: Feb. 21, 2012

(65) Prior Publication Data

US 2012/0302815 A1 Nov. 29, 2012

Related U.S. Application Data

(60) Provisional application No. 61/444,634, filed on Feb. 18, 2011.

(51) Int. Cl.
*A61K 38/00* (2006.01)

(52) U.S. Cl.
CPC ..................................... *A61K 38/00* (2013.01)
USPC .......................................................... 514/1.1

(58) Field of Classification Search
CPC ...................................................... A61K 38/00
See application file for complete search history.

(56) References Cited

PUBLICATIONS

Ciechanover et al., Advanced information on the Nobel Prize in Chemistry, 2004.*
Ayaydin, F. & Dasso, M. (2004) Distinct in vivo dynamics of vertebrate SUMO paralogues. *Mol Biol Cell* 15, 5208-5218.
Brust M, Walker M, Bethell D, Schiffrin DJ, & Whyman R (1994) Synthesis of Thiol-derivatised Gold Nanoparticles in a Two-phase Liquid-Liquid System. *Journal of the Chemical Society, Chemical Communications* 801-802.
Burgess, R. C., Rahman, S., Lisby, M., Rothstein, R., & Zhao, X. (2007) The Slx5-Slx8 complex affects sumoylation of DNA repair proteins and negatively regulates recombination. *Molecular and cellular biology* 27, 6153-6162.
Butterworth, K. T., Coulter, J. A., Jain, S., Forker, J., McMahon, S. J., Schettino, G., Prise, K. M., Currell, F. J., & Hirst, D. G. (2010) Evaluation of cytotoxicity and radiation enhancement using 1.9 nm gold particles: potential application for cancer therapy. *Nanotechnology* 21, 295101, 9 pages.
Chithrani, D. B., Jelveh, S., Jalali, F., van Prooijen, M., Allen, C., Bristow, R. G., Hill, R. P., & Jaffray, D. A. (2010) Gold nanoparticles as radiation sensitizers in cancer therapy. *Radiation Research* 173, 719-728.
Hicke, L., Schubert, H. L., & Hill, C. P. (2005) Ubiquitin-binding domains. *Nature Reviews* 6, 610-621.
Lallemand-Breitenbach V, et al. (2008) Arsenic degrades PML or PML-RARalpha through a SUMO-triggered RNF4/ubiquitin-mediated pathway. (Translated from eng) *Nat Cell Biol* 10(5):547-555.

Mo YY & Moschos SJ (2005) Targeting Ubc9 for cancer therapy. *Expert Opin Ther Targets* 9(6):1203-1216.
Percherancier Y, et al. (2009) Role of SUMO in RNF4-mediated promyelocytic leukemia protein (PML) degradation: sumoylation of PML and phospho-switch control of its SUMO binding domain dissected in living cells. *The Journal of biological chemistry* 284(24):16595-16608.
Prudden, J., Pebernard, S., Raffa, G., Slavin, D. A., Perry, J. J., Tainer, J. A., McGowan, C. H., & Boddy, M. N. (2007) SUMO-targeted ubiquitin ligases in genome stability. *Embo J* 26, 4089-4101.
Sekiyama, N., Ikegami, T., Yamane, T., Ikeguchi, M., Uchimura, Y., Baba, D., Ariyoshi, M., Tochio, H., Saitoh, H., & Shirakawa, M. (2008) Structure of the small ubiquitin-like modifier (SUMO)-interacting motif of MBD1-containing chromatin-associated factor 1 bound to SUMO-3. *The Journal of biological chemistry* 283, 35966-35975.
Song, J., Durrin, L. K., Wilkinson, T. A., Krontiris, T. G., & Chen, Y. (2004) Identification of a SUMO-binding motif that recognizes SUMO-modified proteins. *Proceedings of the National Academy of Sciences of the United States of America* 101, 14373-14378.
Sun, H., Leverson, J. D., & Hunter, T. (2007) Conserved function of RNF4 family proteins in eukaryotes: targeting a ubiquitin ligase to SUMOylated proteins. *Embo J* 26, 4102-4112.
Tatham, M. H., Geoffroy, M. C., Shen, L., Plechanovova, A., Hattersley, N., Jaffray, E. G., Palvimo, J. J., & Hay, R. T. (2008) RNF4 is a poly-SUMO-specific E3 ubiquitin ligase required for arsenic-induced PML degradation. *Nature cell biology* 10, 538-546.
Verma, R., et al. (2004) Ubistatins inhibit proteasome-dependent degradation by binding the ubiquitin chain. *Science* (New York, N.Y) 306, 117-120.
Wang, J., Hu, W., Cai, S., Lee, B., Song, J., & Chen, Y. (2007) The intrinsic affinity between E2 and the Cys domain of E1 in ubiquitin-like modifications.*Mol Cell* 27, 228-237.

(Continued)

*Primary Examiner* — Marcela M Cordero Garcia
*Assistant Examiner* — Kaipeen Yang
(74) *Attorney, Agent, or Firm* — Kilpatrick Townsend & Stockton LLP

(57) ABSTRACT

A composition used to develop a reagent for investigating Ubl-modifications in cellular functions and in the treatment of cancer is provided. The composition comprises gold nanoparticle (AuNP)-ligand conjugates that include at least two components: gold nanoparticles (AuNPs) and modified ubiquitin- or ubiquitin-like interacting motif (UIM or ULIM) mimetics. In one embodiment, the modified ULM mimetic is a modified SUMO interaction motif (SIM) mimetic. According to the embodiments described herein, the compound inhibits ubiquitin- or ubiquitin-like protein (Ubl)-mediated protein-protein interactions and sensitizes cells to ionizing radiation. The modified UIM and ULIM mimetics may be conjugated to the AuNP such that each AuNP is conjugated to a plurality of modified UIM or ULIM mimetics. The modified ULIM mimetics may be conjugated to the AuNP via a thiol group.

12 Claims, 24 Drawing Sheets

(56) References Cited

PUBLICATIONS

Weisshaar Sr, et al. (2008) Arsenic trioxide stimulates SUMO-2/3 modification leading to RNF4-dependent proteolytic targeting of PML. *FEBS Lett* 582(21-22):3174-3178.

You C-C, De M, Han G, & Rotello VM (2005) Tunable Inhibition and Denaturation of α-Chymotrypsin with Amino Acid-functionalized Gold Nanoparticles. *Journal of the American Chemical Society* 127(37):12873-12881.

\* cited by examiner

Mono-Ubl

Poly-Ubl chains

A

B

C

US 8,796,202 B2

MULTI-VALENT POLY-UBL CHAIN INHIBITORS AND METHODS OF USE

PRIORITY CLAIM

This application claims priority to U.S. provisional patent application No. 61/444,634, filed Feb. 18, 2011, the subject matter of which is hereby incorporated by reference, as if fully set forth herein.

STATEMENT OF GOVERNMENT SUPPORT

This application was made with support from National Institutes of Health (NIH) Grant Nos. R01-GM086171 and R01GM074748; National Cancer Institute Grant Nos. P30 CA33572 and F32CA134180; and National Cancer Institute (NCI) Cancer Center Pilot Project Grant No. 5-P30-CA-33572-25. The government has certain rights in this invention.

BACKGROUND

Ubiquitin-like proteins (Ubls) are a growing family of post-translational modifiers that are involved in a diverse array of biological processes. Although Ubiquitin is one of the most well-understood Ubl, several others are now understood to serve many important cellular functions, including: small ubiquitin-like modifier (SUMO), interferon-stimulated gene-15 (ISG15; also known as ubiquitin cross-reactive proteins, UCRP), ubiquitin-related modifier-1 (URM1), neuronal-precursor-cell-expressed developmentally downregulated protein-8 (NEDD8, also called Rub1 in *S. cerevisiae*), human leukocyte antigen F associated (FAT10), autophagy-8 (Apg8) and -12 (Apg12), Fau ubiquitin-like protein (FUB1), MUB (membrane-anchored UBL), ubiquitin fold-modifier-1 (UFM1) and ubiquitin-like protein-5 (UBL5, which is but known as homologous to ubiquitin-1 [Hub1] in *S. pombe*).

Protein-protein interactions mediated by mono-Ubl (ubiquitin and ubiquitin-like proteins) or poly-Ubl modifications are among the most important signalling and regulatory mechanisms that control nearly every aspect of cellular function (1). However, an effective approach to distinguishing poly-Ubl chain mediated from mono-Ubl mediated cellular functions is lacking. In addition to proteasome inhibitors, a small molecule was identified that binds to and alters the conformation of polyubiquitin chains such that their interactions with the proteasome are inhibited (15). However, the negative charge of this small molecule prevents its translocation into cells. Therefore, the identification of inhibitors ubiquitin and ubiquitin-like dependent protein-protein interaction would be useful to study the role of ubiquitination in cellular processes, and for developing therapeutics for viral infection, cancer and other diseases.

SUMMARY

In one embodiment, a composition is provided that may be used to develop a reagent for investigating Ubl-modifications in cellular functions or to treat cancer is provided. The composition comprises gold nanoparticle (AuNP)-ligand conjugates that include at least two components: gold nanoparticles (AuNPs) and modified ubiquitin- or ubiquitin-like interacting motif (UIM or ULIM) mimetics. In one embodiment, the modified ULIM mimetic is a modified SUMO interaction motif (SIM) mimetic. According to the embodiments described herein, the compound inhibits ubiquitin- or ubiquitin-like protein (Ubl)-mediated protein-protein interactions and sensitizes cells to ionizing radiation. The modified UIM and ULIM mimetics may be conjugated to the AuNP such that each AuNP is conjugated to a plurality of modified UIM or ULIM mimetics. The modified ULIM mimetics may be conjugated to the AuNP via a thiol group.

In another embodiment, a method for killing cancer cells is provided. Such a method includes contacting one or more cancer cells with a composition comprising AuNP-ligand conjugates, such as those described above, and exposing the cancer cells to an ionizing radiation source. In another embodiment, a method for increasing radiation sensitivity in cancer cells is provided. Such a method includes contacting one or more cancer cells with a composition comprising gold nanoparticle-ligand conjugates as described above. These methods may be used to treat cancer by producing an effect that enhances the effect of ionizing radiation therapy that is commonly used in cancer treatments.

DETAILED DESCRIPTION

Compositions that inhibit ubiquitin-, or ubiquitin-like protein (Ubl)-mediated protein-protein interactions and sensitize cells to radiation, and methods for their use are provided herein. Such compositions may inhibit any ubiquitin- or Ubl-mediated protein-protein interactions, including, but not limited to, those mediated by small ubiquitin-like modifier (SUMO), ubiquitin cross-reactive protein (UCRP, also known as interferon-stimulated gene-15 ISG15), ubiquitin-related modifier-1 (URM1), neuronal-precursor-cell-expressed developmentally downregulated protein-8 (NEDD8), human leukocyte antigen F-associated (FAT10), autophagy-8 (ATG8) and -12 (ATG12), Fau ubiquitin-like protein (FUB1), MUB (membrane-anchored UBL), ubiquitin fold-modifier-1 (UFM1) and ubiquitin-like protein-5 (UBL5).

Figure 1:
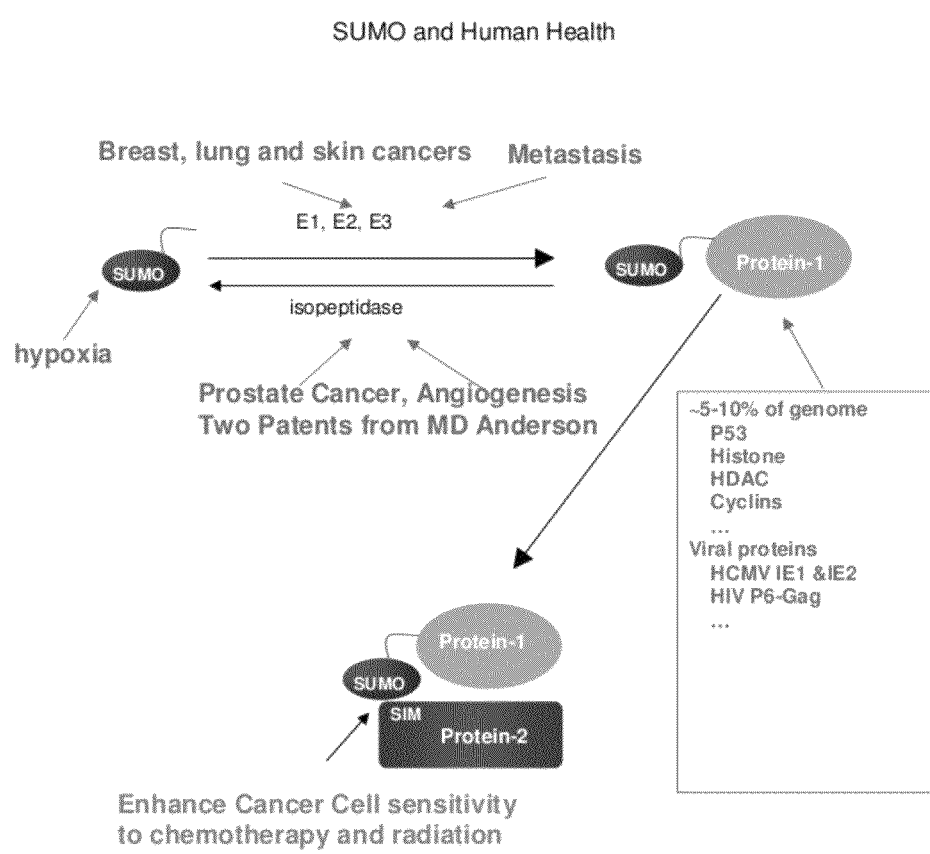
FIG. 1 is a schematic diagram that illustrates SUMO's relation to human health. There are three aspects to the SUMO-mediated processes. The first is the conjugation process, which requires the catalysis by three enzymes, E1, E2 and E3. The modification can be removed by another family of enzymes, known as the isopeptidases. The modified protein acquires a new binding site, and is able to interact with proteins containing the SUMO-binding (or interacting) motif (SBM, SIM). The SUMO substrates include many proteins that are critical for nuclear functions. In addition, viral proteins are subject to this modification. Viral infection often involves hijacking the host post-translational modifications. The enzymes catalyzing the modification have much higher levels in cancer tissues, and in metastasized tumors and have been found to be important for the proliferation of these cancers and for metastasis. An increased level of isopeptidase (Senp1) is shown in prostate cancer, and suppression of Senp1 level by SiRNA can suppress prostate cancer and angiogenesis. Hypoxia also induces high levels of SUMO-1. SUMO-mediated protein-protein interactions appear to be involved in most SUMO-dependent processes.

In some embodiments, the compositions may inhibit SUMO-mediated protein-protein interactions. Post-translational modifications of cellular proteins by the small ubiquitin-like modifier (SUMO) family of proteins have important regulatory mechanisms for vital cellular functions, such as cell cycle progression, DNA damage response and viral infection. SUMO proteins are covalently attached to other proteins in cells to modify their function by a process known as SUMOylation. In mammals, four SUMO paralogues have been identified: SUMO-1, SUMO-2, SUMO-3 and SUMO-4. Covalent conjugation of SUMO proteins to other proteins requires multiple steps that are catalyzed by three types of SUMOylation enzymes, known as E1, E2 and E3 (FIG. 1).

In most cases, Ubl modification serves as a platform for interactions with other proteins. For instance, ubiquitylation dependent processes are mediated by ubiquitin-binding motifs in receptor proteins, such as proteosome (6). SUMO-dependent functions are mediated by a SUMO-interaction motif (SIM, also known as SUMO-binding motif, SBM) on a target protein (7, 8) that serves as receptor for SUMO modified proteins (FIG. 1).

Figure 2:
FIG. 2 shows ubiquitin or ubiquitin-like modifications that may be conjugated to cellular proteins. (A) shows a mono-Ubl chain and (B) shows a poly-Ubl chain.
Figure 2:
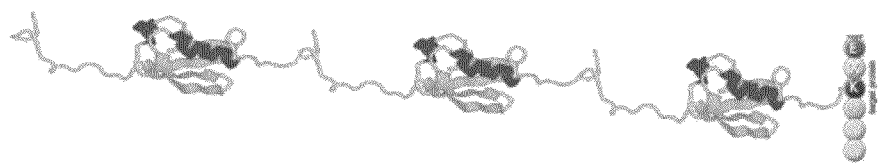
Figure 21:
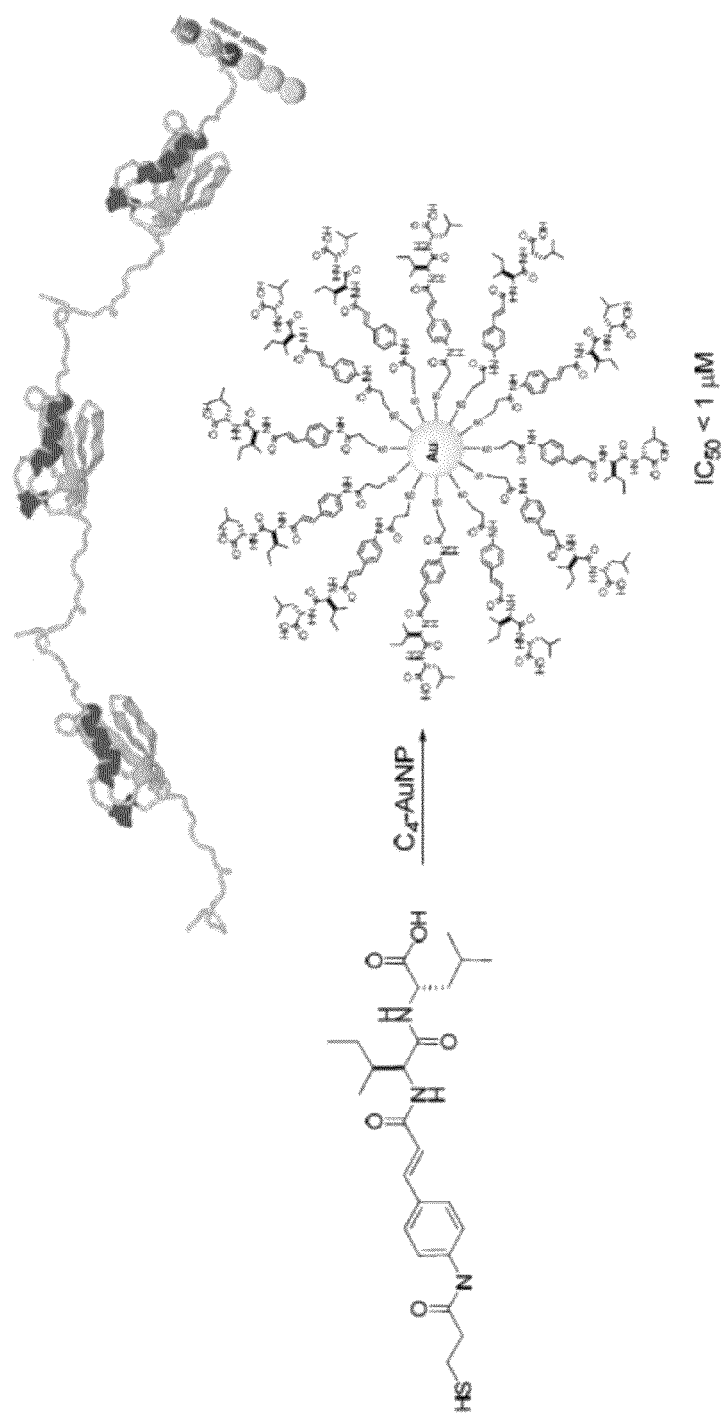
FIG. 21 illustrates that by generating an AuNP conjugate according to the embodiments described herein, poly-Ubl affinity is specifically enhanced by creating multi-valent interactions.

Protein-protein interactions mediated by ubiquitin-like (Ubl) modifications occur as mono-Ubl or poly-Ubl chains (FIG. 2). SUMO-1, SUMO-2 and SUMO-3 play essential roles in cellular response to DNA damage (2). SUMO-2 and -3 are nearly identical, but share less than 50% sequence homology to SUMO-1 (3, 4). A distinction of SUMO-2 and 3 from SUMO-1 is that they carry internal SUMO modification sites at their N-termini, and thus they can form poly-SUMO chains (5), but SUMO-1 usually does not. Poly-SUMO (small ubiquitin-like modifier) chains play important roles in cellular response to DNA damage, such as those caused by cancer radiation therapy. Using SUMOylation as a model system, an approach for using gold nanoparticles (AuNP) as a platform to develop reagents that specifically target poly-Ubl chains was developed. As described herein, a low affinity inhibitor for mono-Ubl effectively inhibits poly-Ubl-mediated protein-protein interaction when the ligand is conjugated to AuNP. The selectivity for poly-Ubl-mediated protein-protein interaction when the ligand is conjugated to AuNP. The selectivity for poly-Ubl chains is due to the AuNP providing a platform for multivalent interactions that result in much higher overall affinity between the AuNP-ligand conjugate and poly-Ubl chains (FIG. 21). The same approach demonstrated for the SUMO proteins can be applied to ubiquitin and other ubiquitin-like modifications.

Recent studies have shown that a SUMO-targeted ubiquitin ligase (STUBL) is important in the DNA damage response, and the ligase specifically recognize poly-SUMO-2/3 chains to ubiquitinate poly-SUMO modified proteins for degradation (9-14). These studies suggest that inhibiting poly-SUMO-2/3 interactions with down-stream effectors, such as STUBL, can inhibit the DNA damage response in response to radiation. However, as mentioned above, an effective approach to disrupt poly-Ubl chain-mediated cellular functions has been lacking.

Figure 3:
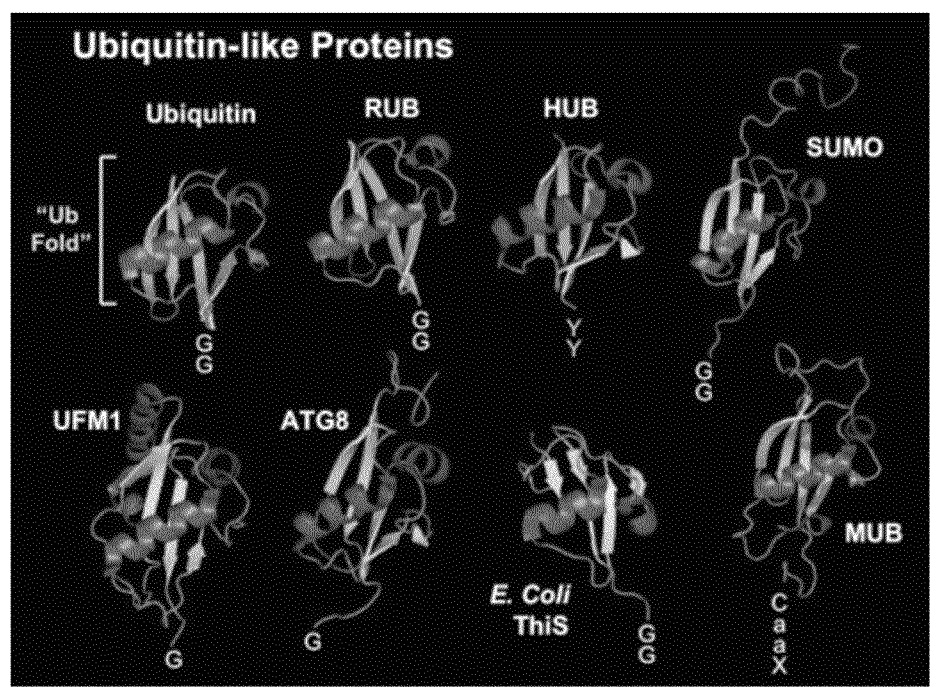
FIG. 3 illustrates that all ubiquitin-like proteins share the same ubiquitin fold ("Ub Fold") structure (see http://vierstra.genetics.wisc.edu/research.sumo.php).

According to some embodiments, the compositions described herein may include one or more Ubiquitin- or Ubiquitin-like interacting motifs (UIM or ULIM) mimetic and at least one radiation sensitizing agent. The UIM or ULIM mimetics described herein may inhibit any protein-protein interactions mediated by ubiquitin or a ubiquitin-like protein because all ubiquitin-like proteins share a structural fold called a "ubiquitin fold" (FIG. 3) FAT10 and UCRP contain two ubiquitin folds. As discussed in the Examples below, the ULIM mimetics described herein bind to the ubiquitin fold (or "binding groove") of SUMO. Because this binding groove is conserved across all ubiquitin-like proteins, the ULIM mimetics described herein may be used to inhibit any protein-protein interactions that are mediated by ubiquitin or ubiquitin-like proteins that have such a binding groove.

Ubiquitin-like proteins that may be inhibited by the ULIM mimetics described herein may include, but are not limited to, small ubiquitin-like modifier (SUMO), ubiquitin cross-reactive protein (UCRP, also known as interferon-stimulated gene-15 ISG15), ubiquitin-related modifier-1 (URM1), neuronal-precursor-cell-expressed developmentally downregulated protein-8 (NEDD8), related to ubiquitin protein (RUB), homology to Ub (HUB), human leukocyte antigen F-associated (FAT10), autophagy-8 (ATG8) and -12 (ATG12), Fau ubiquitin-like protein (FUB1), MUB (membrane-anchored UBL), ubiquitin fold-modifier-1 (UFM1) and ubiquitin-like protein-5 (UBL5).

In one embodiment, the ULIM mimetic is a SUMO interaction motif (SIM) mimetic. The SIM mimetics described herein may interfere with or inhibit the interaction between a mono- or poly-ubiquitinylated protein and an effector protein, thereby suppressing or inhibiting cellular ubiquitin- or ubiquitin like-dependent functions. A mono or poly-ubiquitinylated protein may include proteins that undergo one or more post-translation modifications by ubiquitin or any other ubiquitin-like proteins. In some embodiments, the SIM mimetics described herein may inhibit the interaction between a mono- or poly-Ubl protein and an effector protein such that it inhibits or suppresses the DNA damage response in a cancer cell. For example, in one embodiment, the SIM mimetics may inhibit the interaction between a mono- or poly-SUMOylated protein and an effector protein, thereby suppressing or inhibiting cellular SUMO-dependent functions. Such functions may include, but are not limited to, DNA damage repair, nuclear-cytosolic transport, transcriptional regulation, apoptosis, protein stability, response to stress, and progression through the cell cycle.

SIM mimetics that may be used in accordance with the embodiments described herein may be identified by any suitable method known in the art. SIM mimetics may be identified by any suitable method, including virtual ligand screening methods. For example, the docking program, GLIDE, may be used to search a compound library for compounds that closely match the target binding site. According to some embodiments, SIM mimetics that may be included as part of the compositions described herein includes the following structures:

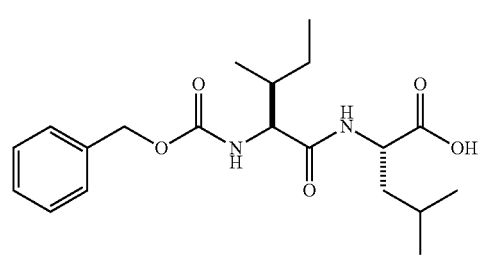

333751

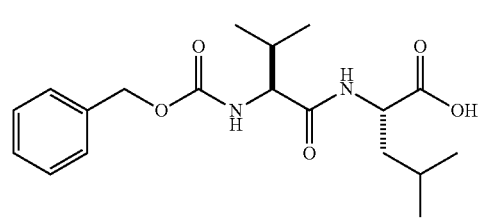

343731

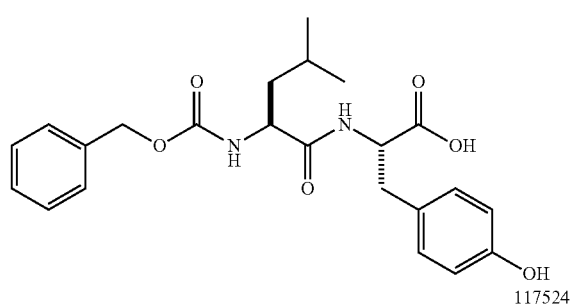

333761

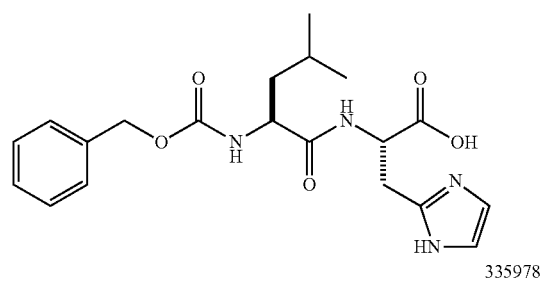

117524

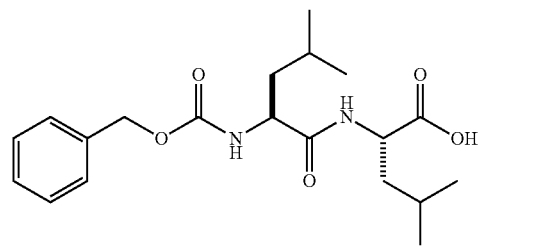

335978

According to some embodiments, the compositions described herein may also include radiation-sensitizing agents. Radiation-sensitizing agents suitable for use in the compositions and methods described herein include, but are not limited to, substances that enhance the effect of radiation or radiotherapy on target cells, such as high atomic number materials. In one embodiment, the radiation-sensitizing agents are gold nanoparticles (AuNPs). Each AuNP can be conjugated to a plurality of SIM mimetics, such as those described above, to form an AuNP-ligand conjugate. In one aspect, each AuNP conjugate includes an AuNP In some embodiments, the SIM mimetics described herein are modified to allow conjugation to AuNPs or other suitable radiation-sensitizing agents. Therefore, in one embodiment, the compositions described herein includes a SIM mimetic-AuNP conjugate, wherein the SIM mimetic portion of the conjugate interferes with or inhibits the interaction between a SUMOylated protein and an effector protein and the AuNP portion of the conjugate enhances the effect of radiation. Such agents are described further below. In one embodiment, the modification includes the addition of a thiol tail. In some embodiment, the thiol tail may comprise a suitable thiol functional group, including, but not limited to:

(1) SH—R and
(2) SH—$(CH_2)_2$—C(O)—NH—R.

The thiol tail allows the modified SIM mimetic to be conjugated to an AuNP by disulfide bonds. In one embodiment, the modified SIM mimetics are thiol derivatives that have the following structure:

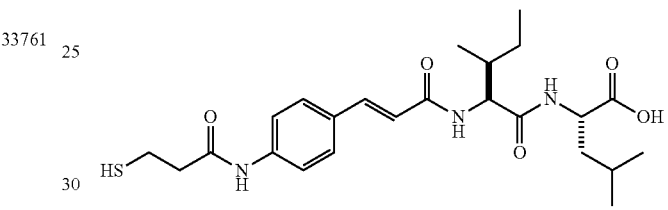

Figure 7A:
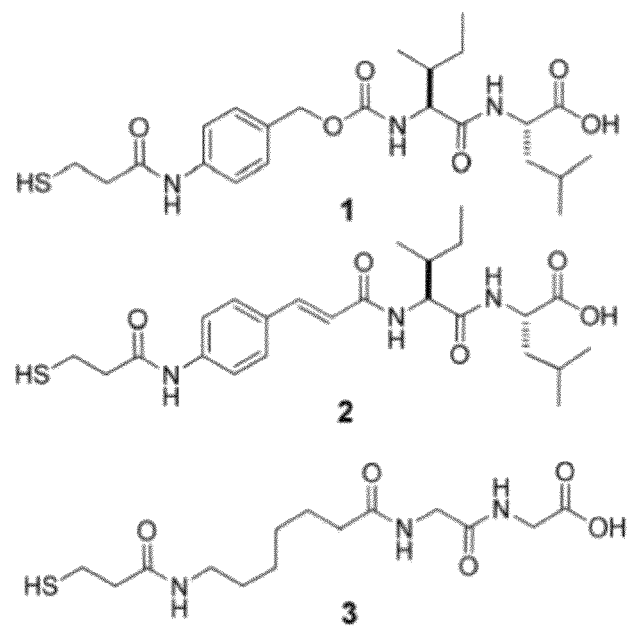
FIG. 7 illustrates the synthesis of an AuNP-ligand conjugate according to the embodiment. (A) Synthesis of thiol mimetics of NCI-333751 for linking to AuNPs. (B) Comparison of binding of the thiol mimetic 2 (red spectrum) and NCI-333751 (green spectrum) to SUMO-3, both at approximately 3:1 of ligand:protein ratio. Both spectra are superimposed with that of free SUMO-3 (black). (C) Construction of the ligand-AuNP conjugates AuNP 4 and AuNP 5. (D) NMR spectrum of 4.
Figure 7B:
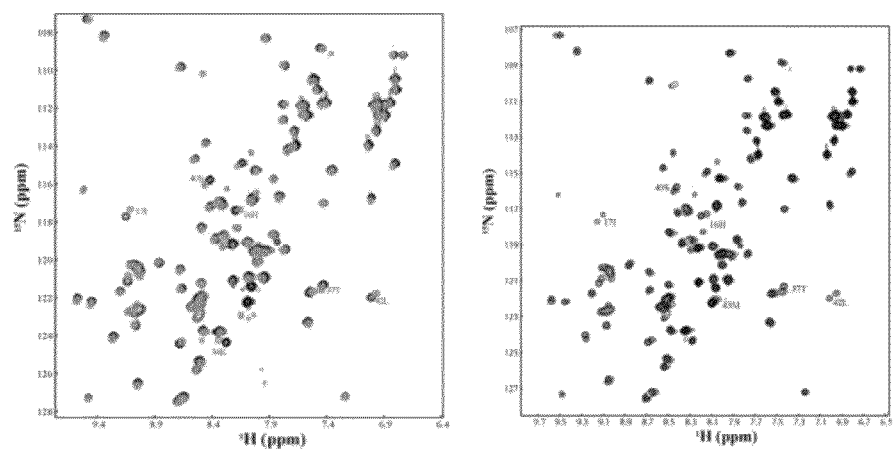
Figure 7C:
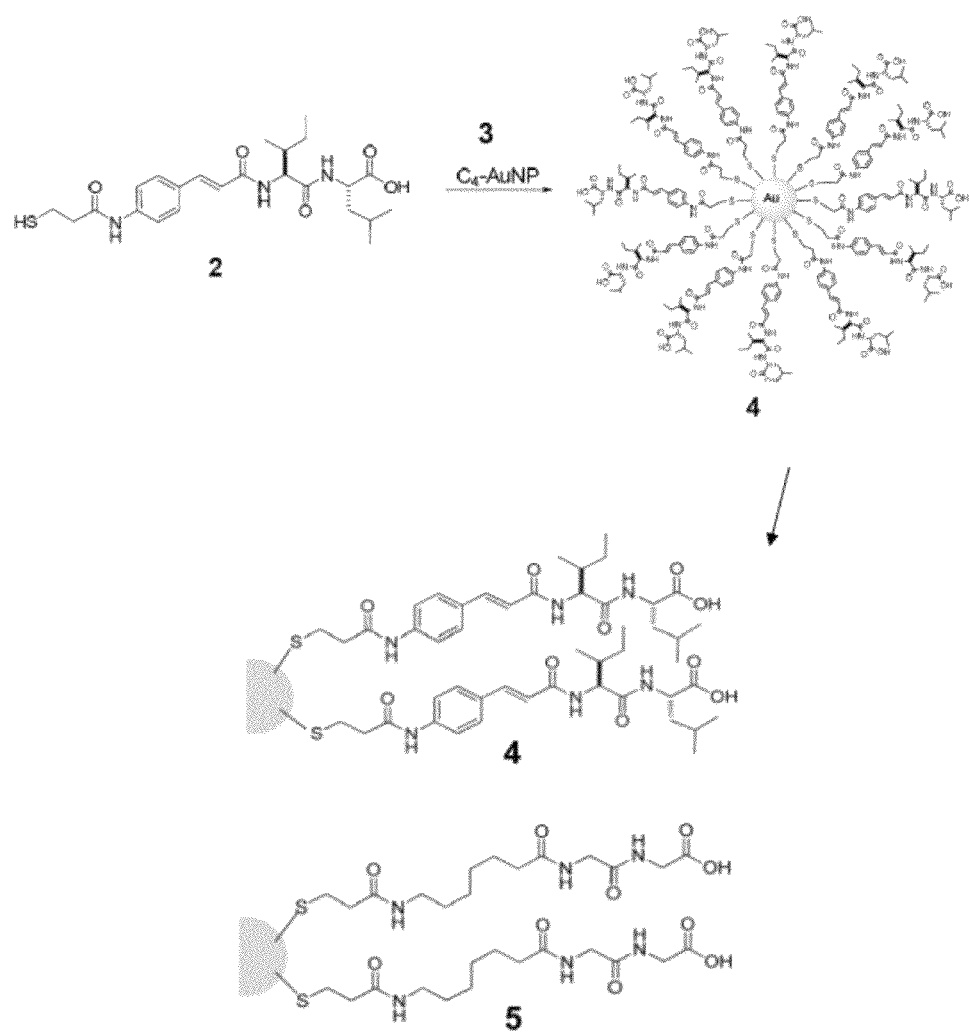

In one embodiment, each AuNP is conjugated to a plurality of modified SIM mimetics to produce a multivalent ubiquitin or ubiquitin-like protein (Ubl) inhibitor with high avidity (see FIG. 7C). As described in the Examples below, SUMO inhibitors, or SIM mimetics (i.e., ligands) were identified, and conjugated to gold nanoparticles. These SUMO inhibitors or SIM mimetics may be used to inhibit any ubiquitin or Ubl protein as described above. This conjugation facilitated selective multi-valent interactions with poly-SUMO-2/3 chains leading to a more efficient inhibition of poly-SUMO-chain-mediated protein-protein interactions than when the inhibitors are used alone. Such AuNP conjugates not only inhibit the DNA damage response mediated by poly-SUMO chains, but also enhance the effects of radiation as described further below. Further, the AuNP-ligand conjugate significantly enhanced the radiation effect in cancer cells but was not toxic to normal cells.

The SIM mimetics, AuNP-ligand conjugates or both may be part of a reagent that is used to study the role of Ubl modifications in cellular functions. Such reagents may be used in a method for inhibiting protein-protein interactions mediated by Ubl modifications, wherein said method may include contacting a cell with or administering to the cell, an effective amount of the reagent. The cell may be of any cell type that is associated with mono- or poly-Ubl modifications. In certain embodiments, the cell type used in the methods for inhibiting a SUMOylation enzyme described herein may be a cell that is part of a population of cells or a biological tissue that is present, in vivo, in a subject having a disease (e.g., cancer) or other physiological or pathological condition associated with mono- or poly-Ubl modifications. This may include a human or animal patient that develops the disease or other physiological or pathological condition or, alternatively, may include an animal or invertebrate model wherein the disease, or physiological or pathological condition may be induced. In other embodiments, the cell type used in the methods for inhibiting protein-protein interactions mediated by Ubl modifications described herein may be a primary, secondary or immortal cell line that is grown in culture. In certain aspects of this embodiment, the method may be used in an in vitro or research setting to investigate the role of SUMOylation in the particular cell, disease, or condition.

The AuNP-ligand conjugates and compositions thereof described above may be used in methods related to the treatment of cancer. Such methods may include administering the AuNP-ligand conjugates or a composition thereof to a subject having cancer. Both ionizing radiation and most chemotherapeutic drugs kill cancer cells by inducing genotoxic stress, fatally damaging the cells' DNA. However, SUMO-mediated or other Ubl-mediated protein-protein interactions may contribute to resistance to these treatments, because they are associated with the DNA damage response to such stresses. Thus, compositions such as those described above that can amplify radiation effects and/or inhibit DNA damage response should be effective in increasing the efficacy of ionizing radiation therapy that is commonly used in cancer treatment.

In one embodiment, the compositions described above may be used in methods for enhancing radiation sensitivity in cancer cells. High atomic number materials such as gold preferentially absorb more X-ray energy than soft tissues, thereby augmenting an ionizing radiation effect when delivered to cells. Recent studies have in fact shown that gold nanoparticles do not cause cellular toxicity, but significantly enhance radiation effect (16, 17). Gold nanoparticles of the size of medium proteins can translocate to cells and are generally thought to be non-toxic to cells due to the inert property of gold (17).

Thus, gold nanoparticles (AuNP) were used as a platform to develop reagents that specifically target poly-SUMO chains and amplify radiation response. As described further in the Examples below, low affinity inhibitors for mono-SUMO were shown to effectively inhibit poly-SUMO (SUMO-2 and -3)-mediated protein-protein interaction when the inhibitor (i.e., the ligand) is conjugated to AuNP. The selectivity for poly-SUMO or other poly-Ubl chains is likely due to the AuNP providing a platform for multi-valent interactions that results in substantially higher overall affinity between the AuNP-ligand conjugate and the poly-Ubl chains. Thus, in some embodiments, the methods for enhancing radiation sensitivity of cancer cells include contacting one or more cancer cells with a composition that comprises AuNP-ligand conjugates as described above. These AuNP-ligand conjugates not only amplify radiation effects, but are also inhibitors of the DNA damage response mediated by poly-Ubl chains, including, but not limited to, poly-SUMO chains.

As discussed above, the binding pocket or groove is conserved across all ubiquitin-like proteins. Therefore, the studies described below demonstrate a strategy to selectively inhibit protein-protein interactions mediated by posttranslational modifications with poly-Ubl, and the conjugates described herein (e.g., AuNP 4) may bind any other Ubl in addition to polySUMOylated proteins. With the rapid development of nanotechnology, a wide variety of nanoparticles has become available. As discussed below, combining the properties of any suitable nano materials with any suitable nanoparticles as platforms for multivalent interactions presents a significant opportunity for development of therapeutic applications.

Therefore, in another embodiment, the compositions described above (e.g., AuNP-ligand conjugates) may be used in methods for killing cancer cells. As previously described, the compositions include two components that enhance the effects of ionizing radiation therapy used in traditional cancer treatments: (1) AuNPs, which sensitize cells to the radiation therapy, and (2), SIM mimetics, which interfere or inhibit the DNA damage response to the radiation therapy. Therefore, according to embodiments described herein, methods for killing cancer cells may include contacting one or more cancer cells with such a composition and exposing the cancer cells to an ionizing radiation source. The radiation source may be from any suitable source used for treating cancer including, but not limited to, X-ray, computed tomography (CT) and positron emission tomography (PET).

The methods described above may be used to treat any cancer or tumor type. Cancers and tumor types that may be treated using the methods described herein include but are not limited to bone cancer, bladder cancer, brain cancer, breast cancer, cancer of the urinary tract, carcinoma, cervical cancer, colon cancer, esophageal cancer, gastric cancer, head and neck cancer, hepatocellular cancer, liver cancer, lung cancer, lymphoma and leukemia, melanoma, ovarian cancer, pancreatic cancer, pituitary cancer, prostate cancer, rectal cancer, renal cancer, sarcoma, testicular cancer, thyroid cancer, and uterine cancer. In addition, the methods may be used to treat tumors that are malignant (e.g., cancers) or benign (e.g., hyperplasia, cyst, pseudocyst, hamartoma, and benign neoplasm).

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

In some embodiments, AuNP-ligand conjugates and compositions thereof described above are part of a pharmaceutical composition. The pharmaceutical composition may include one or more AuNP-ligand conjugates and a pharmaceutically acceptable carrier. In some embodiments, the pharmaceutical composition/SUMO inhibitor may be administered in combination with one or more DNA-damaging therapies. In this case, the AuNP-ligand conjugates may sensitize the target cells/cancer cells to the DNA-damaging therapy. Thus, the DNA-damaging therapy is more effective, and allows the use of lower doses, thereby minimizing or eliminating harm to healthy cells.

A "pharmaceutically acceptable carrier" may refer to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof, described in further detail below. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

Pharmaceutically acceptable carriers are well known in the art and include, for example, aqueous solutions such as water or physiologically buffered saline or other solvents or vehicles such as glycols, glycerol, oils such as olive oil or injectable organic esters, or emulsions such as oil/water emulsions or a triglyceride emulsion, various types of wetting agents, tablets, coated tablets and capsules. A suitable pharmaceutically acceptable carrier may be selected taking into account the chosen mode of administration.

A pharmaceutically acceptable carrier can also contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art will know that the choice of a pharmaceutically acceptable carrier, including a physiologically acceptable compound, depends, for example, on the route of administration of the composition.

In one preferred embodiment, the pharmaceutical carrier may be a liquid and the pharmaceutical composition would be in the form of a solution. In another equally preferred embodiment, the pharmaceutically acceptable carrier is a solid and the pharmaceutical composition is in the form of a powder or tablet.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient. In tablets, the active-ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Besides containing an effective amount of the AuNP-ligand conjugates described herein the pharmaceutical compositions may also include suitable diluents, preservatives, solubilizers, emulsifiers, adjuvant and/or carriers.

The compound can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

Optimal dosages to be administered may be determined by those skilled in the art, and will vary with the particular compound in use, the severity of the disease state, drug combination(s), reaction sensitivities, and response to therapy. Additional factors depending on the particular subject being treated, including the general health of the subject, the age, weight, gender and diet of the subject, and time and frequency of administration, will result in a need to adjust dosages. Administration of the AuNP-ligand conjugates or pharmaceutical composition thereof may be effected continuously or intermittently. In any treatment regimen, the AuNP-ligand conjugates or pharmaceutical composition may be administered to a patient either singly or in a cocktail containing other therapeutic agents, compositions, or the like, including, but not limited to, tolerance-inducing agents, potentiators and side-effect relieving agents. Preferred potentiators include monensin, ammonium chloride, perhexyline, verapamil, amantadine, and chloroquine. All of these agents are administered in generally-accepted efficacious dose ranges such as those disclosed in the Physician's Desk Reference, 41st Ed., Publisher Edward R. Barnhart, N. J. (1987), which is incorporated herein by reference.

The term "subject" may refer to a human or any other animal, animal model or invertebrate model having a condition, a disease, a cell, or a population of cells that may be treated or used accordance with the methods or with the compounds or compositions described herein. In one embodiment, the subject is a human subject having a disease or condition, such as those described herein. In other embodiments, the subject is any other animal having such a disease or condition, including an animal model used as a research tool that is developed to have the disease or condition or has one or more aspects, attributes, symptoms, or other variables associated with the disease or condition. As such, the AuNP-ligand conjugates described herein may be used as research tools. Such animals or animal models may include, but are not limited to, mice, rats, rabbits, monkeys, pigs, dogs, cats, and birds. In another embodiment the subject may be any other vertebrate or invertebrate model that can be used as a research tool including, but not limited to, a fish (e.g., zebrafish), an insect (e.g., *drosophila*), nematode (e.g., *c. elegans*), mollusk (e.g., *aplesia californicus*).

In some embodiments, a cell or population of cells grown in culture may be used in accordance with the methods or with the compounds or compositions described herein. The cell or population of cells may be derived from or cultured from one or more subjects described above, and may used as a research tool in accordance with the embodiments described herein.

Administering one or more compounds or compositions described herein to the subject, cell or population of cells to investigate one or more mechanisms or other aspects of a condition or disease described herein; or for investigating the effect of one or more compounds or compositions described herein when administered to the cell, population of cells or subject.

The term "effective amount" as used herein refers to an amount of a compound that produces a desired effect. For example, a population of cells may be contacted with an effective amount of a compound to study its effect in vitro (e.g., cell culture) or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a compound and adjusting the dosage accordingly. For additional guidance, see Remington: The Science and Practice of Pharmacy, $21^{st}$ Edition, Univ. of Sciences in Philadelphia (USIP), Lippincott Williams & Wilkins, Philadelphia, Pa., 2005, which is hereby incorporated by reference as if fully set forth herein.

The cancer cells used in the methods described above may be from an in vitro culture system, or they may exist as part of a tumor (e.g., a primary tumor, a metastatic tumor, a malignant tumor or a benign tumor). When the cells are part of a tumor, the composition may be administered in a therapeutically effective amount to a subject having cancer The compositions described herein may be administered by any suitable route of administration. A "route of administration" may refer to any administration pathway known in the art, including but not limited to aerosol, enteral, nasal, ophthalmic, oral, parenteral, rectal, transdermal (e.g., topical cream or ointment, patch), or vaginal. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Identification of SIM Peptides and SIM Mimetics

Materials and Methods

Virtual ligand screening. Docking was performed with GLIDE 3.5 (31, 32) in standard precision mode (SP). The E-model scoring function was used to select the top compounds. A grid box having a default size (18×18×18 Å$^3$) was centred on three core amino acids in the SIM peptide (D3, V4 and I5) (7, 8). Default parameters were used and the following constraints were included during grid generation. First, intermolecular hydrogen bond constraints included two of the three sites on SUMO: K32 and K34. In addition, hydrophobic interactions with F31 and I33 of SUMO-3 are also included in the constraints. The Maestro user interface (Schrodinger, LLC, New York, N.Y.) was used to prepare the GLIDE docking calculations and visualize the results. To eliminate molecules that adopt excessively strained conformations in their docked pose, top compounds with internal energy greater than 1.5 kcal/mol/rotatable bond were eliminated.

NMR studies. All NMR samples contained 10 mM phosphate buffer (pH 7.0) in 90% H$_2$O/10% D2O. NMR spectra were acquired at 25° C. on a Bruker 500 Hz NMR spectrometer. All chemicals were dissolved in DMSO. Heteronuclear Single Quantum Coherence (HSQC) spectra were acquired at SUMO:compound ratios of 1:3 or 1:10 for the top scored compounds from virtual ligand screening. Both SUMO-1 and SUMO-2 were examined for their interactions with the compounds. The HSQC spectra were acquired for the protein alone, the protein with addition of 2% DMSO, and the protein in complex with a compound and 2% DMSO. The dissociation constant K$_d$ was estimated by titrating the compound to SUMO-2, followed by recording HSQC spectra at protein: compound ratios of 1:1, 1:2, 1:3, 1:4, 1:5, 1:6, 1:7 and 1:20.

Results

Figure 20:
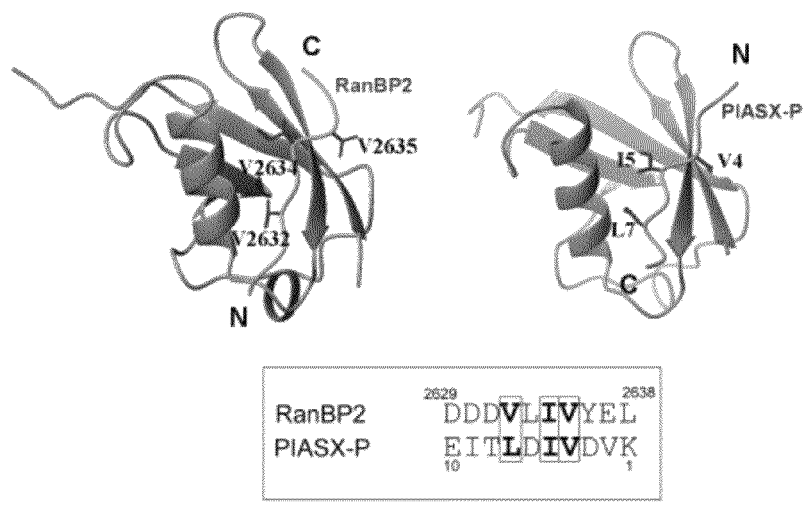
FIG. 20 shows SUMO-Interacting Motifs (SIMs) for RanBP2 and PIASX-P. SUMO and ubiquitin contain a docking site for protein-protein interaction. Using NMR-based structural analysis, the SUMO-recognition motif was identified. A structural analysis was made of SUMO in complex with SIM from various proteins. This analysis explains why a consensus sequence motif can not be found by sequence alignments alone. First, the SIM is very short, because it binds to SUMO in an extended conformation. Second, the bound orientations can be opposite from each other depending on the nature of the sequence. Proper sequence alignment requires reversal of some sequences, which is impossible without the knowledge of the three-dimensional structure. The consensus sequence is only revealed using structure-based sequence alignment, as described herein.

Identification of Peptide Analogues that Mimic the SIM. To identify a small molecular ligand of SUMO, virtual ligand screening was carried out based on a SIM in order to inhibit SUMO-mediated down-stream effects. The structure of SUMO-3 in complex with a SIM peptide was constructed by transferring the SIM sequence from the protein PIASx that is in the structure of its complex with SUMO-1 to the mimeticous site in the structure of SUMO-3 (FIG. 20) (8). The SIM sequence (KVDVIDLTIE; SEQ ID NO:1) from PIASx has the highest affinity for and binds all SUMO isoforms among characterized SIM sequences, and binds all SUMO isoforms with dissociation constants between 4-8 μM (7). The analogous interactions of the SIM with different SUMO paralogues were determined by NMR analysis of the SIM peptide in complex with SUMO-3 (data not shown) and later confirmed by an independent NMR study (18). The SIM peptide forms a β-strand that extends the existing β-sheet in SUMO. Previous studies have shown that the core consensus sequence of SIM consists of 5 amino acid residues binding to a shallow groove of SUMO (8). Hydrophobic interactions between the SIM and I33 and F31 of SUMO-3 appear to be some of the most important. In addition, the SIM peptide forms backbone hydrogen bonds with SUMO-3, which extends the β-sheet of SUMO.

Constrained docking was employed to find potential SIM mimetics. The initial virtual screening was performed by considering the shape and hydrophobic interactions of the SIM binding groove of SUMO-3. However, this approach did not yield any hits. A second screening was carried out that included backbone hydrogen bonding constraints with K32 and K34 of SUMO-3, because hydrogen bonds provide high specificity in protein-protein and protein-ligand interactions. Known examples of the significance of hydrogen bonds include those stabilizing the double-strand of DNA and secondary structures of proteins. Other than the two hydrogen bonds, a hydrophobic region was defined that includes the contact areas of sidechains of I33 and F31. The GLIDE program was used to search the 250,000 compound library provided by the Developmental Cancer Therapeutics program of the National Cancer Institute. The docked structures were chosen using E-model scoring function of Cvdw, which is the sum of the van der Waals (Evdw) and electrostatic interaction energy terms (Eelec). A group of peptide mimetics was identified among the top hits (FIG. 4), and their GLIDE scores are shown in Table 1 below.

TABLE 1

Binding interactions derived from docking the compounds to SUMO-3.

| Chemical NCI | HBond | vdW$^a$ | Coul$^a$ | Emodel$^a$ | CvdW$^a$ |
|---|---|---|---|---|---|
| 333751 | 4 | −25.3 | −13.2 | −75.4 | −38.6 |
| 343731 | 3 | −24.0 | −12.7 | −75.5 | −36.7 |
| 333761 | 4 | −24.1 | −15.5 | −79.8 | −38.2 |
| 117524 | 5 | −21.6 | −16.6 | −76.9 | −38.2 |
| 335978 | 3 | −27.0 | −10.5 | −74.2 | −37.5 |

Figure 4:
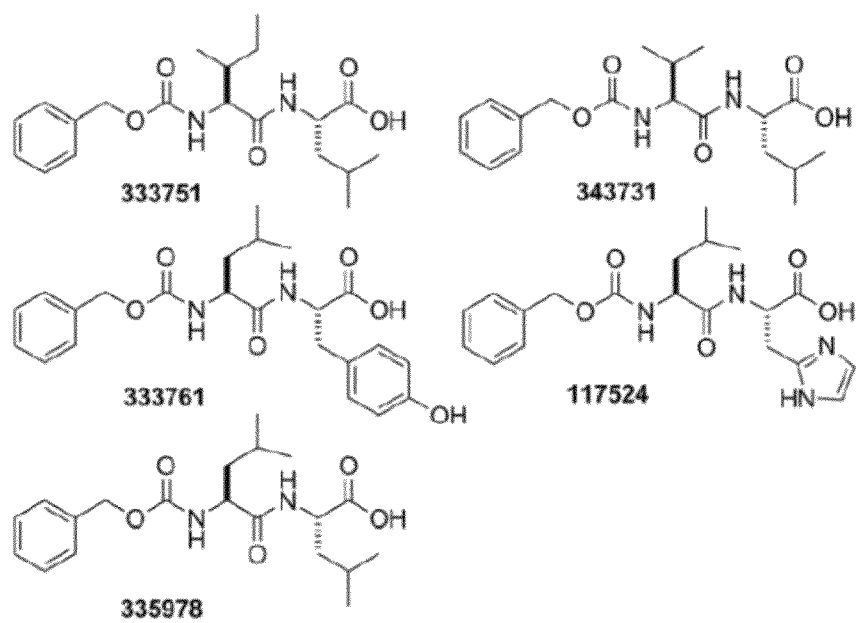
FIG. 4 shows the top hits identified from the GLIDE program search of NCI compound library. The NSC compound identifier number is shown for each compound.

HBond: number of hydrogen bond
vdW: van der Waals interaction
Coul: Coulumb interaction
CvdW: vdW + Coul
$^a$in the unit of kcal/mol The characteristics of this group of peptide mimetics are consistent with of the several known characteristics of SUMO-SIM interactions. It was shown previously that β-branched amino acid sidechains, such as Val and Ile, as well as aromatic residues have been shown to have a preference for β-strand conformation (19). As seen in FIG. 4, the sidechains of the identified analogues favor β-strand conformation. In addition, the group shown in FIG. 4 contain the proper backbone for hydrogen bond formation with SUMO that mimics the SIM. Furthermore, the hydrophobic sidechains as well as the phenyl groups of the group shown in FIG. 4 can form hydrophobic interactions with the shallow groove on SUMO.

Figure 5:
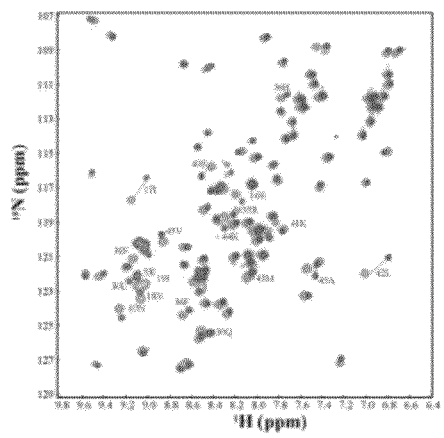
FIG. 5 shows a family of compounds that binds to SUMO-3 in the same groove that binds the SUMO interaction motif (SIM). (A) Superimposed HSQC spectra of SUMO-3 free (green) and in complex with 333751 (red) at 1:10 of protein:ligand ratio. (B) Residues of SUMO-3 that show significant chemical shift perturbation in the HSQC spectrum are indicated in yellow in the structure of SUMO-3. (C) The $^1$H chemical shift of Leu42 of $^{15}$N-labeled SUMO-3 was monitored as a function of added compound 333751. The $K_d$ of the complex was determined by a regression curve fitting of the chemical shift change as a function of the ligand:protein ratio.
Figure 5:
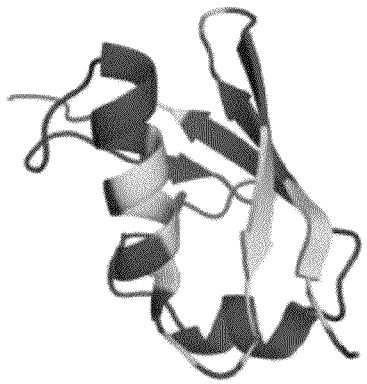
Figure 5:
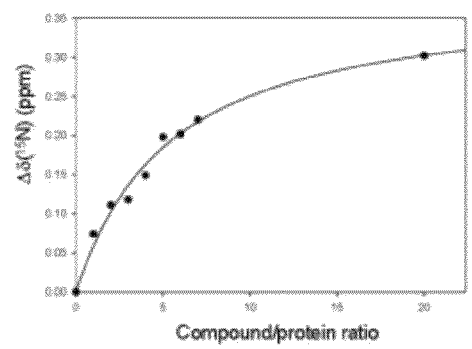
Figure 6:
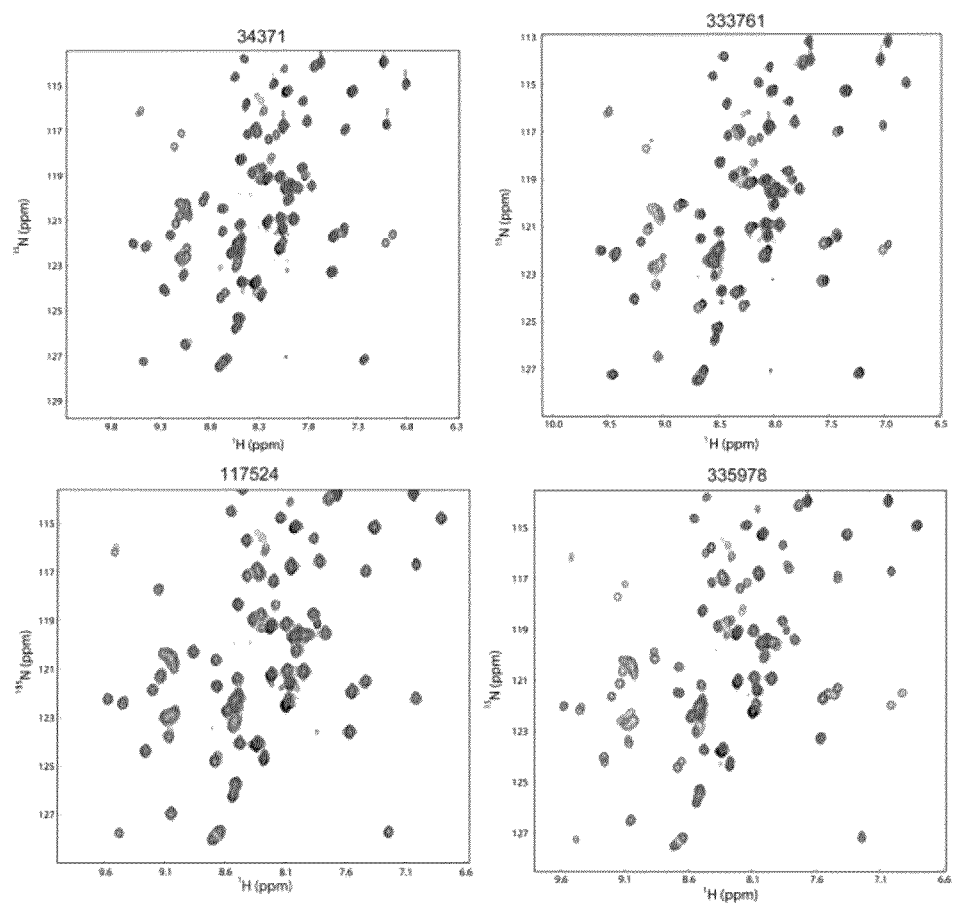
FIG. 6 is an overlay of the HSQC spectra of SUMO-3, free (black) and in complexes with each of the compounds (red) shown in FIG. 4 at ligand:protein ratios of approximately 3:1.

Interactions of the compounds shown in FIG. 4 with SUMO-1 and SUMO-3 were verified by NMR chemical shift perturbation analysis. These compounds generated negligible chemical shift perturbations (CSP) on SUMO-1, but much larger and specific chemical shift perturbations on SUMO-3 (FIGS. 5A and 6). Compound 333751 was chosen for further development, because its binding affinity was among the strongest as estimated by chemical shift perturbation, although all compounds have similarly wad affinities (FIGS. 5A, 6 and 7B). Based upon resonance assignments of SUMO-2 and -3, the lead compounds were observed to bind into the same groove as the SIM peptide (FIG. 5B). Chemical shift perturbation was used to estimate the binding affinity of the representative compound, 333751, to SUMO-3 (20). The $K_d$ of 333751 for binding SUMO-3 is 1.2±0.4 mM (FIG. 5C). Thus, the affinity of this compound to SUMO-2 is more than 200 fold lower than that between the PIASx SIM and SUMO-2. This is not surprising given the much smaller size of the compound than the 10 amino acid residue SIM peptide. The SIM-binding groove on SUMO is very shallow and lacks a deep pocket (8). Since there is a lack of high affinity ligands to bind shallow surface pockets of proteins, it is unlikely that a high affinity small molecule ligand for the SIM binding surface of SUMO can be found.

Example 2

Synthesis of the AuNP-Ligand Conjugate

Materials and Methods

In addition to those described in Example 1 above, the following materials and methods were used.

Synthesis of derivatives 2 and 3. All amino acids, O-(6-Chlorobenzotriazol-1-yl)-N,N,N',N'-tetramentyluronium hexafluorophosphate (HCTU), and 2-chloro chlorotrityl resin were obtained from EMD Biosciences (Novabiochem). All other synthesis reagents were obtained from commercial sources. $^1$H NMR spectra were obtained on a Varian 400 MHz spectrometer and TMS was used as an internal reference. Derivative 2 (FIG. 7A) was constructed on 2-chlorotrityl resin loaded with Fmoc-Leu-OH at 0.8 mmol/g. Fmoc-Ile-OH, Fmoc-cinnaminic acid (21) and 3-(t-butoxycarbonylthio)propanioc acid (22) were sequentially coupled on using standard Fmoc synthesis conditions using HCTU (3 eq) and diisopropylethylamine (8 eq). The compound was cleaved from resin and deprotected with 95% trifluoroacetic acid/2.5% $H_2O$/2.5% triisopropylsilane. The cleaved derivative 2 was purified via reverse phase HPLC (Agilent C-18 prep column 21.5×150 mm) using 20-60% acetonitrile in a water gradient and lypholized. The negative control, 3, was constructed in a similar manner as 2 with 2-chlorotrityl resin loaded with Fmoc-Gly-OH, Fmoc-7-aminoheptanoic acid and 3-(t-butoxycarbonylthio)propanioc acid.

Figure 8:
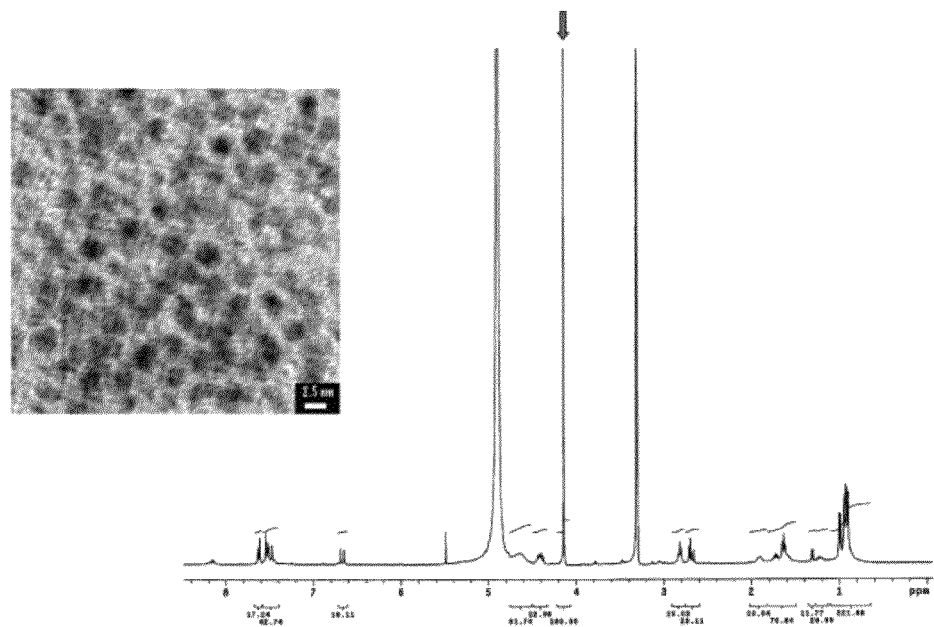
FIG. 8 shows an image of the AuNP by transmission electron microscopy (left) and the NMR spectrum of ligand conjugated AuNP with ferrocene as an internal standard (right). The ferrocene signal is indicated by an arrow.

Loading derivative 2 onto AuNP. The AuNP-ligand conjugate was synthesized according to a procedure described by You et al. (36): C4-AuNP (7 mg) was combined with of derivative 2 or 3 (14 mg) in 1 mL of dichloromethane and equilibrated for 4 d. The precipitated solid was collected via filtration (fine fritted funnel), rinsed with chloroform and dried in vacuo. The nanoparticle suspension was air-dried on the specimen grid and observed using a TECNAI 12 transmission electron microscope (FIG. 8, left inset panel). To conjugate a small amount of biotin onto AuNP 4 or 5, C4-AuNP (6 mg) was combined with derivative 2 (10 mg) or 3 (8 mg) and thiol-biotin (2 mg; Nanoscience Instruments, CMT015), equilibrated for 4 d, and purified as described above. Although NMR spectra demonstrated that derivative 2 or 3 was conjugated to AuNP, biotin signal was not observable by NMR, indicating that the ratio of derivative:biotin on AuNP was more than 9:1. Conjugated biotin was detected by FITC-conjugated streptavidin.

Results

Multivalency of low affinity binding can achieve an overall high affinity. Thus, it was determined whether such specific but low affinity compounds can form high affinity interactions with poly-SUMO chains by creating multi-valent interactions. Gold nanoparticles (AuNPs) were chosen as a platform for multivalent interactions, because of their commercial availability and inert qualities. Compound 333751 (FIG. 4) was modified for conjugation to an AuNP by adding a thiol tail. Initial attempts to synthesize thiol derivative 1 (FIG. 7A) proved to be problematic, as cleavage from the resin also resulted in cleavage of the aminobenzyl carbamate moiety, generating only trace amounts of the derivative 1. Because of this instability, the aminobenzyl carbamate was replaced by a more hydrolysis resistant isostere, 4-aminocinnamic acid, as contained in 2. The E-double bond geometry should mimic the S-trans configuration of the carbamate in 1. Derivative 2 was constructed on 2-chloro-chlorotrityl resin using standard Fmoc-synthesis conditions. N-Fmoc-cinnamic acid (21) and 3-(tbutoxycarbonylthio) propanioc acid (22) were then coupled to install the thiol tail. Finally, resin cleavage and thiol deprotection lead to recovery of thiol derivative 2 in good yield. A control 3 that contains the same backbone but lacks side chains was also designed and synthesized using a similar strategy (FIG. 7A).

Binding of derivative 2 to SUMO-1 and SUMO-3 was also examined and compared to that of compound 333751. FIG. 7B shows a side-by-side comparison of SUMO-3 binding to compound 333751 and the derivative 2 at SUMO:ligand ratio of 1:3. Both compounds induced chemical shift perturbation on the same surface of SUMO-3 and to a similar extent, indicating that their modes of interaction with SUMO-3 are nearly identical.

Figure 7D:
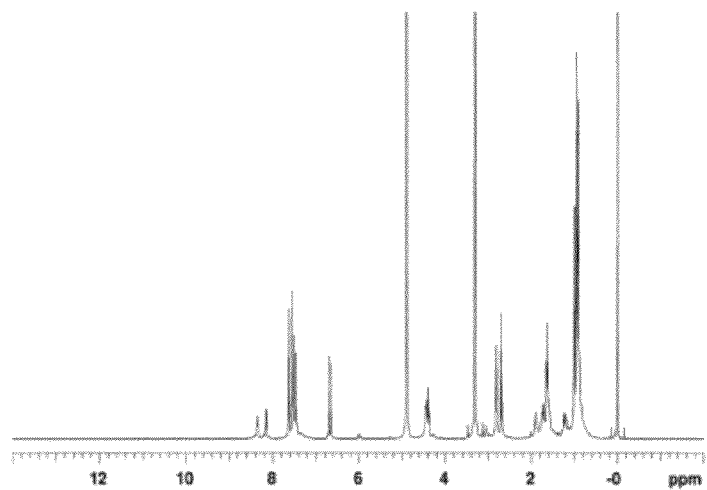

Derivatives 2 and 3 conjugated to gold nanoparticles (AuNPs) were constructed from C4-alkanethiol AuNPs (FIG. 7C) (23). Derivative 2 or 3 was equilibrated with C4-AuNP in dichloromethane for 4 days according to previously described procedures (24). The precipitated ligand-AuNP conjugate 4 or 5 (AuNP 4 or 5) was collected via filtration. NMR analysis (FIGS. 7D and 8) indicated that derivation was complete and all butanethiol groups on the AuNP were displaced.

The number of ligands on each gold nanoparticle was determined using a similar procedure as previously described (25). Briefly, the size of the nanoparticles was confirmed by transmission electron microscopy (FIG. 8) to be 2.0-2.5 nm. The molecular weight and molar amount of AuNPs were calculated by assuming ideal spherical particles. The number of ligands per AuNP was determined using ferrocene as an internal standard for calibration of ligand NMR signal intensity (FIG. 8) as previously described (25). Each conjugated nanoparticle was estimated to contain approximately 100 ligands. The sharp NMR resonances also indicated that the conjugated ligands maintained significant conformational flexibility (FIG. 8).

Example 3

Inhibition of Poly-SUMO Chain-Mediated Protein-Protein Interactions

Materials and Methods

In addition to those described in Examples 1 and 2 above, the following materials and methods were used.

Cell culture. The HeLa-SUMO2 cell line that stably expresses His-tagged SUMO2 was a kind gift from Dr. Ronald Hay (University of Dundee, UK). MCF-7, HeLa and HeLa-SUMO2 cells were maintained in DMEM (GIBCO) supplemented with 10% (v/v) fetal bovine serum (FBS) (Irvine Scientific), 1 mM sodium pyruvate, nonessential amino acids, and 100 µg/ml of penicillin/streptomycin (Irvine Scientific) and Normocin (InvivoGen). MCF-10A cells were maintained in DMEM with 10% (v/v) FBS, penicillin/streptomycin (100 µg/ml), nonessential amino acids, EGF (20 ng/ml), hydrocortisone (0.5 µg/ml), insulin (10 µg/ml) and Cholera toxin (100 ng/ml). PC3 cells were maintained in RPMI with 10% (v/v) FBS and penicillin/streptomycin (100 µg/ml). RWPE1 cells were maintained in Keratinocyte-SFM media from Invitrogen. All cells were incubated at 37° C. in a humidified chamber supplemented with 5% $CO_2$.

Poly-SUMO chain formation. Poly-SUMO chains were synthesized by an in vitro SUMOylation reaction (4.375 µM GST-SUMO-3 and His-SUMO-3, 40 nM Ubc9 and E1, and 5 mM ATP in a 100 µl reaction). The reaction was carried out at 37° C. for 4 h and then diluted to 1 mL with phosphate buffered saline (PBS). Poly-SUMO chains were first separated from the His-SUMO-3 monomer by glutathione affinity chromatography. The eluted poly-SUMO chains were subsequently separated from the GST-SUMO-3 monomer by Ni-NTA chromatography. The eluted poly-SUMO chains were dialyzed and concentrated.

Purification of GST-WT-SIM and GST-SC-SIM. GST-tagged wild-type (GST-WT-SIM) or scrambled SIM sequence (GST-SC-SIM) was subcloned into the pGex4T-S expression vector (Amersham) and over-expressed as an N-terminal GST fusion protein in *Escherichia coli* strain BL21 (DE3) (Invitrogen) at 37° C. in LB media. Once the OD A595 nm reached 0.6, isopropyl 1-thio-δ-Dgalactopyranoside (IPTG; 1 mM) was added to the media and the cells were grown for an additional 4 h at 37° C. Harvested cells were re-suspended in lysis buffer (PBS, pH 7.4, 150 mM sodium chloride, 5 mM β-mercaptoethanol [βME], 1× BugBuster and Benzonase Nuclease [Novagen, 1000×]), and the pellet was isolated by centrifugation (15,000 g×30 min). Proteins were dissolved in 8M urea and renatured in a buffer containing PBS, pH 7.4, 150 mM sodium chloride, 10 mM 2-mercaptoethanol and 5% glycerol. The GST-tagged proteins were then conjugated to glutathione agarose resin and eluted in a buffer containing 10 mM glutathione.

Biotin-AuNP pull-down. HeLa cells were collected by centrifugation (500 g, 4° C., 15 min) and washed four times in ice-cold PBS containing 200 mM iodoacetamide. Next, cells were incubated on ice in cell extraction buffer (10 mM HEPES, pH 7.9, 1.5 mM $MgCl_2$, 10 mM $KCl_2$, 0.07% NP40, complete protease inhibitor cocktail tablets (Roche) and 100 mM iodoacetamide) for 15 min. Cells were disrupted by sonication on ice (6×20 s with an 18% amplitude by a Virtis Sonicator). Cellular debris was removed by centrifugation at 17,000×g and the supernatant was pre-cleared with strepta-vidin agarose beads before incubation with biotinylated AuNPs. Biotin-AuNP 4 or biotin-AuNP 5 (5 µg) was incubated with 10 mg of pre-cleared HeLa whole-cell extract at 4° C. overnight. After a brief centrifugation, streptavidin agarose beads (20 µg) were added to the solution, which was then incubated at 4° C. for 2 h. After incubation, the agarose was centrifuged (4,500×g, 5 min) to remove the unbound proteins. The agarose was then washed three times in cell extraction buffer and the isolated proteins were eluted with Laemmli sample buffer. The protein samples were separated by SDS-PAGE and analyzed by Western blot according to standard procedures.

Figure 19:
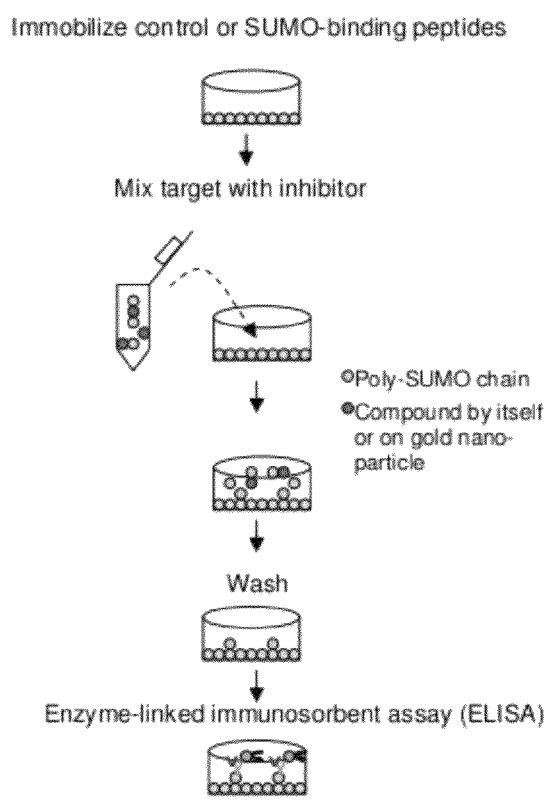
FIG. 19 is a schematic diagram illustrating a SIM pull-down experiment according to an embodiment described in Example 3 below.

SIM pull-down. Individual wells in 96-well EIA/RIA plates (Costar) were pre-coated with GST13 WT-SIM or GST-SC-SIM (5 µg) at 4° C. for overnight. After pre-coating, the plate was blocked with 5% BSA at 37° C. for 2 h. SUMO-1, SUMO-3 or polymer SUMO-3 (5 µg) was mixed with 0.5% BSA and free ligand, AuNP or ligand-conjugated AuNP at various concentrations, as indicated (FIG. 9), before addition to the EIA plate. After the SUMO-chemical compound or SUMO-gold particle mixture was added to the wells, the plate was incubated at 37° C. for 3 h. Unbound protein was removed by washing the wells with 1×PBS containing 1% BSA three times. Anti-SUMO-1 rabbit polyclonal antibody or anti-SUMO-3 rabbit polyclonal antibody was then added to the wells and the plate was incubated at 4° C. overnight. The wells were then washed three times with 1×PBS containing 1% BSA, after which, horseradish peroxidase (HRP) conjugated goat anti-rabbit antibody (1:2000) was added to the wells and the plate was incubated at 37° C. for 1 h. After three washes with 1×PBS containing 1% BSA, 3,3',5,5'-tetramethylbenzidine (TMB) and hydrogen peroxide (H2O2) (1:1) were added to the wells, generating a color reaction. The plate was read at 450 nm by an ELISA reader after the reaction was stopped by addition of phosphoric acid. Quantifications of all SIM pull-downs were scaled by measurement of GST-WT-SIM pull-down (100%) and GST-SCSIM pull-down (0%). A schematic diagram of a SIM pull-down experiment is illustrated in FIG. 19.

Antibodies. All antibodies were obtained from commercial sources, including mouse anti-SUMO-1 (Abgent), rabbit anti-SUMO2 and 3 (Abcam), mouse anti-Flag M2 (Sigma), rabbit anti-PML (Santa Cruz Biotech), and mouse anti-β-actin (Sigma) antibodies.

Results

Although the individual compounds shown in FIG. 4 may not have sufficient affinity for SUMO-2 or 3 to compete effectively with most SIM sequences (having $K_d$ values ranging from 10 to 100 µM), an AuNP conjugate (with as many as 100 ligands per gold nanoparticle) allows for multi-valent interactions between the gold nanoparticle with multiple SUMO molecules in a poly-SUMO chain.

Figure 9:
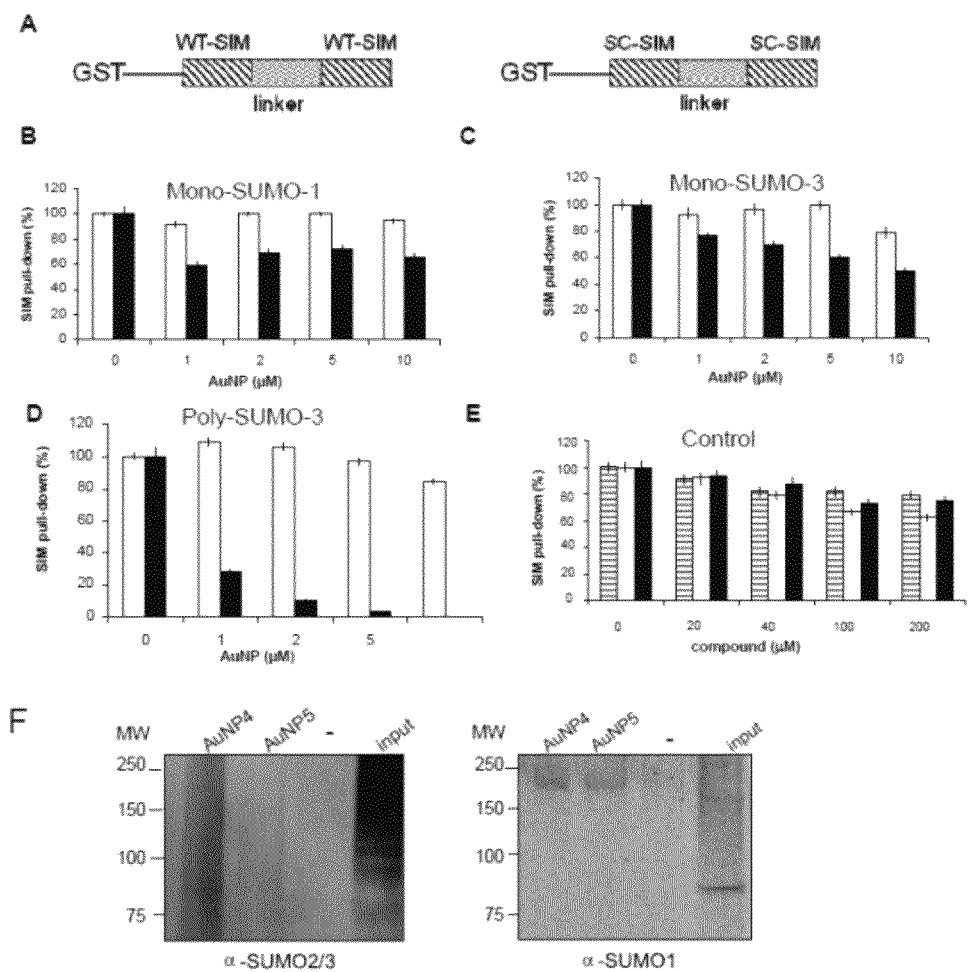
FIG. 9 illustrates the inhibitory effect of the ligand conjugated AuNP 4 on poly-SUMO chain mediated protein-protein interactions. (A) Design of the SUMO-interacting motif (SIM) and control peptides. To target poly-SUMO-chain-mediated protein-protein interactions more effectively, a construct containing two SIMs separated by the sequence between the SIMs from the protein RNF4 was designed. In addition, a control was designed that contained two copies of the scrambled (SC) sequence of the SIM separated by the same linker. (B-C) AuNP conjugated with (■) or without (□) ligand were used to compete with the interactions between SIM and SUMO-1 (B), or SIM and SUMO-3 (C). The quantifications of all the SIM pull-down were scaled by the measurement of pull-down by the GST-tagged wild type-SIM peptide (100%) and GST-tagged control peptide (same amino acid content but with a scrambled sequence) (0%). (D) AuNP 4 significantly inhibits SIM-poly SUMO chain interaction. AuNPs with (■) or without (□) conjugated ligand 2 were used to compete with the interactions between SIM and poly-SUMO-3 chains. (E) The competition of protein-protein interactions between SIM and SUMO1 (dashed bars), SIM and SUMO3 (open bars) and SIM and poly SUMO chains (filled bars) by free derivative 2. (F) Western blot analysis of proteins pulled down by steptavidin agarose beads using an anti-SUMO 2/3 (Left) or anti-SUMO-1 (Right) antibody, showing that biotin conjugated AuNP 4 preferentially binds to polySUMO 2/3 conjugates in HeLa cell lysates. The input fraction represents 6% of inputs.
Figure 10:
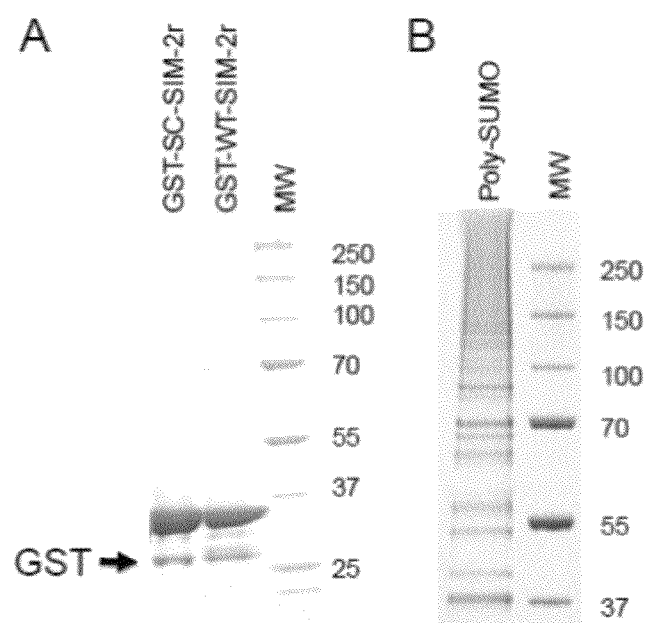
FIG. 10 shows purification of GST-WT-SIM and GST-SC-SIM (A). A small amount of GST was co-purified with the GST-fusion proteins. (B) shows poly-SUMO-3 chains were purified by glutathione affinity chromatography and then by Ni-NTA affinity chromatography. Molecular weight markers (MW) are shown to the right of each gel.

To investigate the efficacy of the AuNP-conjugated ligands 4 at inhibiting poly-SUMO-chain-mediated protein-protein interactions, a poly-SUMO binding peptide was designed as follows. The PIASx SIM was selected because this sequence has ~10 fold higher affinity for all SUMO isoforms than other characterized SIM sequences (7). This SIM sequence was used to replace two major SIM sequences in the protein rfp1, which is a ubiquitin ligase specifically recognizing poly-SUMO modified proteins and ubiquitylates these proteins in DNA damage response (11, 14). In this manner, a strong poly-SUMO-chain binding peptide was designed (FIG. 9A). In addition, a control was designed that contained two copies of the scrambled (SC) sequence of the SIM separated by the same linker (FIG. 9A). The GST-fusion SIM proteins were expressed and purified to greater than 90% homogeneity (FIG. 10A)

The SIM and control peptides were used in pull-down assays to determine the inhibitory effects of the conjugation of inhibitor to AuNPs. Poly-SUMO-3 chains were synthesized by enzymatic reactions of GST-tagged SUMO-3 with His-tagged SUMO-3 followed by affinity purification with glutathione and then Ni-NTA beads (FIG. 10B). The amount of SUMO pulled down by the SIM peptide was detected by enzyme-linked immunosorbent assay (ELISA) in an EIA microtiter plate. Ligand-conjugated AuNP 4 does not efficiently inhibit binding between the monomers of SUMO-3 or SUMO-1 and the tandem-SIM containing peptide (FIGS. 9B and 9C), likely because the ligand has a much lower affinity (with Kd in the mM range as described above) than the PIASX SIM sequence used for pull-down. On the other hand, the same concentration of AuNP 4 was highly effective in inhibiting the interaction between poly-SUMO-3 chain and the tandem-SIM peptide (FIG. 9D) and had an $IC_{50}$ less than 1 μM. It is difficult to accurately estimate the binding affinity between AuNP 4 and poly-SUMO chains. Similar to naturally occurring poly-SUMO or poly-ubiquitin chains, the in vitro synthesized poly-SUMO chains are a mixture of different lengths. As such, the binding affinity likely varies with the length of SUMO chains. Based on the concentrations of SUMO chains and the experimental design, it was determined that the $IC_{50}$ value is likely larger than the average $K_d$ value of the complex between AuNP and SUMO chains. AuNP that is not conjugated with derivative 2 does not have such inhibitory effect (FIG. 9D). In addition, without conjugation to the AuNP, derivative 2 was not significantly inhibitory to the interactions between single SUMO-1 or SUMO-3 and the SIM peptide, nor did it inhibit poly-SUMO chain and SIM interactions (FIG. 9E).

To further investigate the specificity of AuNP 4 for poly-SUMO-2/3 chains, both AuNP 4 and 5 were conjugated with a small portion of biotin, using thiol-biotin. NMR data demonstrated the successful conjugation of ligands 2 and 3 to AuNP, and the presence of a small portion of biotin conjugated to AuNP was detected by FITC-conjugated streptavidin. Biotin-conjugated AuNP 4 and 5 were used to pull down SUMOylated proteins from HeLa cell extracts with streptavidin agarose beads, followed by immunoblotting with an anti-SUMO-1 or anti-SUMO-2/3 antibody. Biotin-conjugated AuNP 4, but not biotin-conjugated AuNP 5, pulled down poly-SUMO-2/3 conjugates (FIG. 9F). AuNP 4 and 5 do not appear to pull down significantly different amounts of SUMO1 conjugates. The faint signal seen with anti-SUMO1 antibodies in both the AuNP 4 and AuNP 5 pull-down lanes may be nonspecific. This result further demonstrates the specificity of AuNP 4 for poly-SUMO-2/3-modified proteins.

These results confirmed the selectivity of AuNP 4 in inhibiting poly-SUMO-3-chain-mediated protein-protein interactions. First, the ligand specifically targets the SIM-binding site of SUMO instead of other hydrophobic patches that are involved in binding the E1 and E2 enzymes. This was demonstrated by NMR chemical shift perturbation (FIGS. 5A and 7B). Non-specific interactions will not produce specific chemical shift perturbations in a localized site on a protein surface. Second, the ligand conjugated AuNP specifically competes with a peptide containing tandem SIM motifs, but not the control peptide of the same amino acid composition. Thus, the hydrophobic butylthiol groups on the control AuNP do not effectively bind SUMO (FIG. 9).

Poly-Ubl chains are usually long and contain more Ubl modules than necessary for binding receptor proteins. Although RNF4 contains two SIM sites and presumably binds two SUMOs in a chain (2), poly-SUMO chains formed in vitro and in vivo are generally much longer (28). Similarly, binding proteosome requires a chain of 4 ubiquitins (29), but poly-ubiquitin chains formed in vitro and in vivo are generally much longer (30). The Ubl chains are usually flexible. The high efficacy of the AuNP 4 is likely due to its ability for three and higher valent interactions of derivative 2, which are expected to be stronger than bi-valent interactions with the strongest SIM sequence designed in this study. With the extensive conformational flexibility of the conjugated ligands and poly-SUMO chains, such lengths would allow the binding of multiple SUMO modules in a chain.

Example 4

Effect on Inhibition of Poly-SUMO Chain-Mediated Protein-Protein Interactions in Cells Materials and Methods
In addition to those described in Examples 1 to 3 above, the following materials and methods were used Subcellular location of AuNPs. HeLa cells were seeded on an 8-well chambered coverglass (LabTekII) one day before AuNP treatment. Biotin-AuNP 4 and -AuNP 5 (4 μM) were incubated with HeLa cells for 24 h at 37° C. in a humidified chamber supplemented with 5% $CO_2$. Cells were then washed twice with PBS and fixed with 4% formaldehyde for 10 min at room temperature. Subsequently, cells were permeabilized with 0.1% Triton X-100 for 20 min and blocked in PBS containing 5% BSA and 0.1% Tween for 30 min. Streptavidin-FITC was diluted in PBS with 1% BSA (1:1000, EMD Millipore) and incubated with the cells for 1 h at room temperature. After three washes with PBS containing 1% BSA, cells were incubated with 0.1 μg/ml DAPI for 20 min. After three washes with PBS containing 1% BSA, cells were then mounted in Vectashield mounting medium and images were collected using a fluorescence microscope (AX10, Zeiss).

Flag-RNF4 protein expression and coimmunoprecipitation. pCMV-Flag-RNF4 plasmid DNA, gift from Dr. Peter Schultz (The Scripps Research Institute), was transfected into HeLa-SUMO2 cells using Lipofectamine LTX (Invitrogen) according to the manufacturer's instruction. Twenty-four hours after DNA transfection, the Flag-RNF4 expressing cells were first treated with 4 μM of C4-AuNP, AuNP 4 or 5 for 24 h and then exposed to 1 μM arsenic trioxide for 1 h. Whole-cell extracts were obtained in cell lysis buffer (300 mM NaCl, 50 mM Tris (pH 7.5), 0.5% NP-40, 1 mM EDTA, protease inhibitor cocktail (Roche), 100 mM iodoacetamide and 1 mM PMSF). For co-immunoprecipitation (co-IP), the whole-cell extract was first pre-cleared by incubation with protein G Dynabeads (Invitrogen) for 2 h at 4° C., and then the pre-cleared lysate (containing 2.5 mg of total cellular protein) was incubated with a mouse anti-Flag antibody (5 μg) overnight at 4° C. After brief centrifugation, the anti-Flag antibody and its associated proteins were isolated by using protein G Dynabeads. The precipitates were then washed six times with co-IP buffer (50 mM Tris-HCl pH7.5, 150 mM NaCl, 0.05% Triton-X100, 10 mM iodoacetamide) and analyzed by Western blot.

Arsenic treatment and immunofluorescence assay. For arsenic treatment and immunofluorescence experiments, HeLa-SUMO2 cells were seeded on coverslips one day before treatments with AuNPs and arsenic C4-AuNP, AuNP 4 or 5 was added to cells 1 h before exposure to 1 μM $As_2O_3$ for 1, 6, and 24 h. Cells were then fixed with 4% formaldehyde for 10 min at room temperature. Subsequently, cells were permeabilized with acetone and methanol mix (1:1) for 10 min and blocked in PBS containing 5% BSA and 0.1% Tween for 30 min. The mouse anti-PML antibody was diluted in PBS with 1% BSA (1:200; Abcam) and then added to the cells for 1 h. After three washes with PBS containing 1% BSA, cells were incubated with Alexa Fluor 555 donkey anti-mouse IgG (Invitrogen) and 0.1 µg/ml DAPI for another hour. After three washes with PBS containing 1% BSA, cells were mounted in Vectashield mounting medium. Images were collected using a fluorescence microscope (Axio; Zeiss). Protein samples from cells treated as described above were denatured by Laemmli sample buffer and then separated by SDS-PAGE. The proteins were then transferred to PVDF membrane and detected by Western blot.

Results

Figure 11:
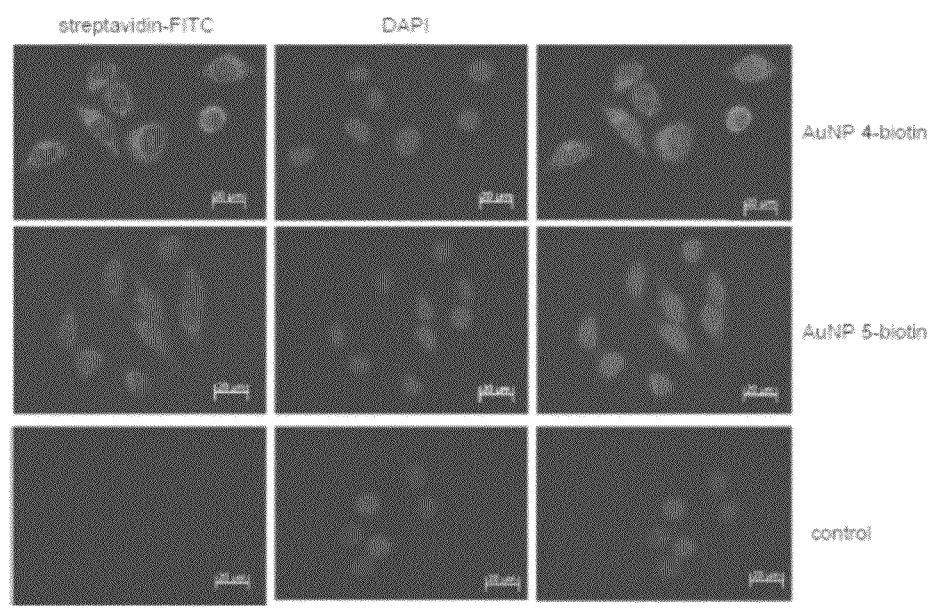
FIG. 11 shows subcellular localization of biotinylated AuNPs. HeLa cells were treated with biotinylated AuNP 4 or 5 for 24 h and the AuNPs were visualized with FITC-conjugated streptavidin (green). Cell nuclei were visualized with DAPI (blue). Cells without AuNP treatment were the control. Bar, 20 μm.

Localization of AuNP 4 and 5 was detected by FITC-conjugated streptavidin (FIG. 11). Fluorescence microscopy indicated that both AuNP 5 and AuNP 4 localized to both the cytoplasm and nucleus. However, AuNP 4 consistently formed brighter foci in the nuclei (FIG. 11). The foci do not completely colocalize with the PML nuclear bodies that are known to contain poly-SUMO2 and 3 conjugates. The nature of the foci that are not colocalized with the PML nuclear bodies requires further investigation. These observations demonstrate that both AuNP conjugates can permeate cells and localize to the nucleus.

Figure 12:
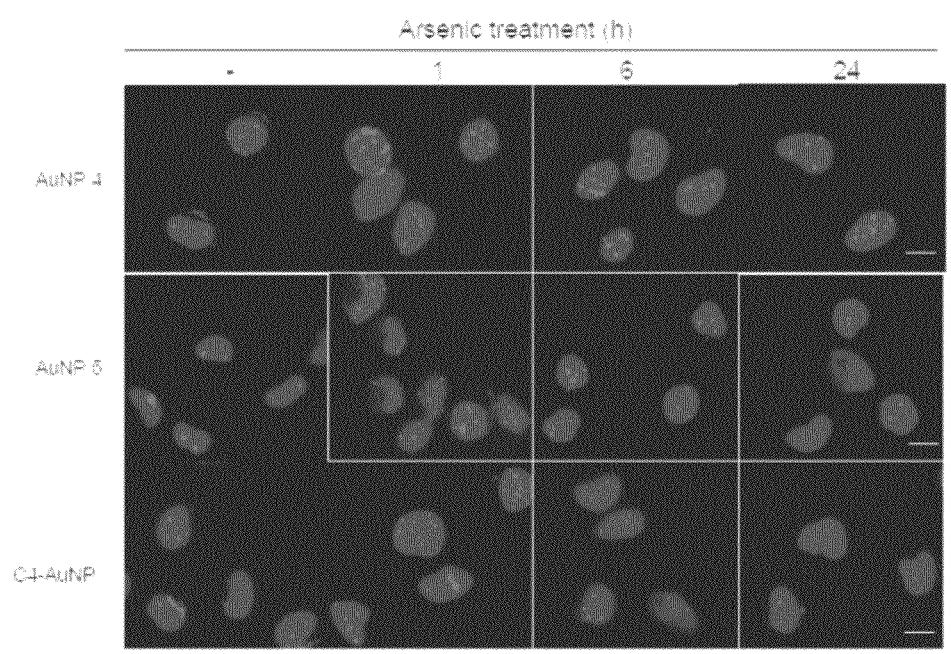
FIG. 12 illustrates the effect of AuNP 4, 5 and C4-AuNP on arsenic trioxide induced PML degradation. PML bodies were monitored in HeLa-SUMO2 cells treated with AuNPs (4 μM) for 1 h before exposure to 1 μM arsenic trioxide for 1, 6, or 24 h. Cells were then fixed and immunostained with an anti-PML antibody (red) and stained with DAPI (blue). Bar, 10 μm.
Figure 13:
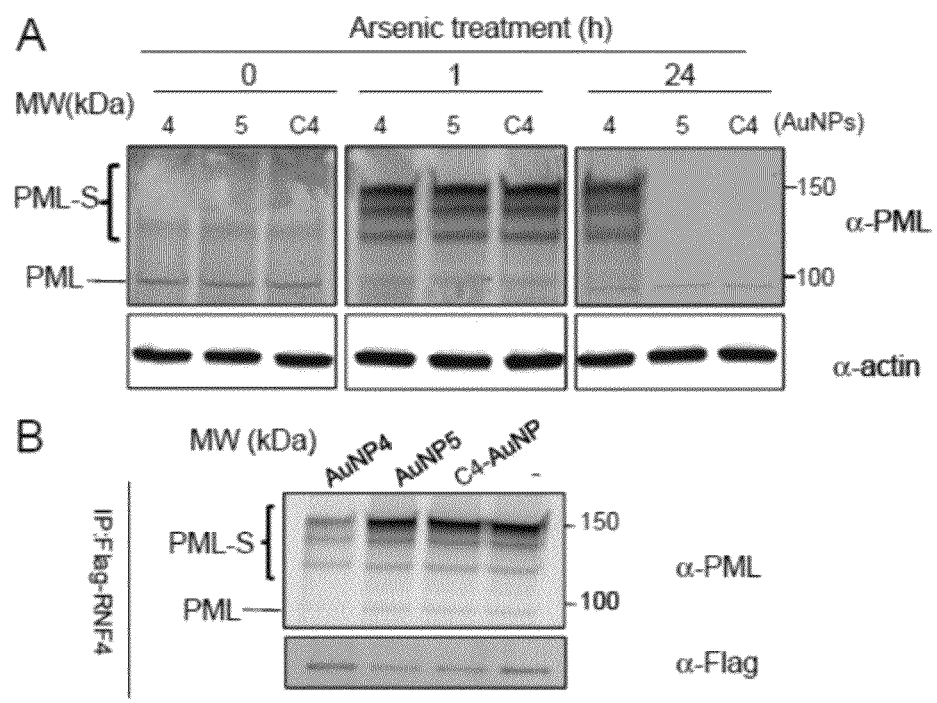
FIG. 13 shows a comparison of the inhibitory effect of AuNP 4 with the two AuNP controls on arsenic trioxide induced PML degradation (A). Western blot analysis of PML protein modification and degradation in HeLa-SUMO2 cells treated with C4-AuNP or AuNP 4 or 5 (4 μM) were exposed to 1 μM arsenic trioxide for 1 or 24 h. (B) shows AuNP 4 inhibited protein-protein interactions between SUMOylated PML and RNF4. HeLa-SUMO2 cells were transfected with a plasmid expressing Flag-tagged RNF4, and after 24 h, were treated with C4-AuNP, AuNP 4 or 5 (4 μM) for 24 h followed by exposure to 1 μM arsenic trioxide for 1 h. The Flag-tagged RNF4 protein was immunoprecipitated using an anti-Flag antibody and its association with PML protein was analyzed by Western blot. In both panels A and B, unmodified PML bands and SUMO modified PML bands (labelled with PML-S) are indicated.

To investigate whether AuNP 4 inhibits SUMO-mediated protein-protein interactions in cells, it was evaluated whether it inhibited arsenic-induced degradation of PML protein. In acute promyelocytic leukemia, PML forms a fusion protein with the retinoic acid receptor alpha (RAR). Arsenic trioxide (As2O3) can effectively treat this disease by inducing poly-SUMO-chaindependent ubiquitylation and proteasomal degradation of the PML-RAR fusion protein (2, 26, 27, 30). The tandem repeats of SIM in RNF4, as discussed above, are responsible for recognition of the poly-SUMOylated PML to target it for ubiquitylation and degradation by the proteasome. Thus, this is a well-established mechanism that specifically depends on poly-SUMOylation mediated protein-protein interactions and is suitable for analysis of AuNP 4 inhibition of SUMO-mediated protein-protein interactions. Arsenic induced an initial increase in PML body formation on both cells treated with AuNP 4 or the control C4-AuNP, as observed previously (2). The number of PML nuclear bodies in control (C4-AuNP)-treated cells decreased significantly over time, but not in the AuNP 4-treated cells. The difference was most pronounced after 24 h of treatment (FIG. 12). To further validate this finding, Western blot analysis was conducted, including both C4-AuNP and AuNP 5 as controls. Because AuNP 5 was a much more expensive control, most experiments were conducted using C4-AuNP as a control, which required that both controls be compared to validate C4-AuNP as a control. Treatment of all AuNP-treated cells with $As_2O_3$ led to a significant increase in PML SUMOylation (higher molecular weight bands in FIG. 13A) after 1 h, indicating that AuNP, by itself, does not exert a nonspecific effect. In contrast, after 24 h arsenic treatment, AuNP 4-treated cells had significant higher levels of modified PML than AuNP 5- and C4-AuNP-treated cells (FIG. 13A). This suggests that AuNP 4 specifically inhibits SUMOylation-dependent PML degradation by inhibiting poly-SUMO-mediated protein-protein interactions between PML and RNF4 in cells. To further demonstrate that AuNP 4 inhibits the interaction of SUMOylated PML with RNF4, coimmunoprecipitation (IP) experiments were conducted using HeLa cells that stably expressed SUMO-2. After overnight treatment with C4-AuNP, or AuNP 4 or 5, cells were exposed to $As_2O_3$ for 1 h, followed by co-IP. RNF4 pulled down much less SUMOylated PML in AuNP 4-treated cells than in C4-AuNP- and AuNP 5-treated cells (FIG. 13B). Again, both controls produced similar results.

These findings further demonstrate the specificity of AuNP 4 at inhibiting poly-SUMO2/3-mediated protein-protein interactions by targeting the SIM-binding surface of SUMO-2/3. The ligand specifically targets the SIM-binding site of SUMO instead of other hydrophobic patches that are involved in binding the E1 and E2 enzymes, as demonstrated by NMR chemical shift perturbation (FIGS. 5A and 7B). Although binding of the proteosome requires a chain of 4 ubiquitins (28), polyubiquitin chains formed in vitro and in vivo are generally much longer (29). Typically, poly-Ubl chains contain more Ubl modules than necessary for binding receptor proteins. Therefore, the potency of AuNP 4 is likely due to binding of multiple SUMO proteins in a chain. The Ubl chains are usually flexible, and the extensive conformational flexibility of the conjugated ligands and poly-SUMO chains would allow the binding of multiple SUMO modules in a chain with AuNP 4.

Example 5

Effect on Cell Proliferation and Radiation Sensitization of AuNP 4

Materials and Methods

In addition to those described in Examples 1-3 above, the following materials and methods were used.

Cell culture. MCF-7 cells were maintained in DMEM (GIBCO) supplemented with 10% (v/v) fetal bovine serum (Irvine Scientific), 1 mM sodium pyruvate, nonessential amino acids and 100 µg/ml of penicillin/streptomycin (Irvine Scientific) and Normocin (InvivoGen). MCF-10A cells were maintained in the DMEM with 10% (v/v) fetal bovine serum, penicillin/streptomycin (100 µg/ml), nonessential amino acids, EGF (20 ng/ml), Hydrocrotisone (0.5 µg/ml), Insulin (10 µg/ml) and Cholera toxin (100 ng/ml).

Cell proliferation assay. $1 \times 10^3$ MCF-7, MCF-10A, PC3 or RWPEI cells were plated in a well of a 96-well plate one day before treatment with AuNPs to allow cells to reach 50% confluency. One hour before radiation or doxorubicin treatment, C4-AuNP (control) or AuNP 4 was added to the cells at 0, 0.1, 1, 2 and 4 µM contractions. For the radiation sensitization assay, cells were irradiated at 4 Gy and returned to incubator for further 48 hours incubation. For the doxorubicin sensitization assay, cells were exposed to 2 µM doxorubicin for 48 hours. The CellTiter 96 AQueous One Solution Cell Viability Assay kit (Promega) was used to analyze cell viability, according to the manufacturer's instructions.

Clonogenic Assay. One day before AuNP treatment, $2 \times 10^2$ of MCF-7 cells were seeded for nonirradiation or $2 \times 10^3$ cells were seed for irradiation in a well of a six-well plate. Control AuNP and C4-AuNP were added to MCF-7 cells at 0, 0.1, 1 and 2 µM contractions. The cells were either irradiated at 4 Gy or not after one hour of AuNP treatment and then returned to the incubator and incubated for 12 days until the colonies formed. The colony was fixed and visualized by a mixture of 6.0% glutaraldehyde and 0.5% crystal violet (34).

Comet assay. MCF-7 cells were grown on 24-well plates to reach 60% confluency. Each well was then treated with either 0.2% DMSO, 2 µM C4-AuNP, or 2 µM AuNP 4 and incubated at 37° C. for 24 h before irradiation. Cells received either no irradiation or 4 Gy irradiation (Cs137 irradiator) followed by incubation at 37° C. for 30 min or 2 h. Cells were gently removed using sterile rubber scrapers. Suspended cells were centrifuged at 700×g for 5 min, aspirated, and resuspended in ice-cold autoclaved PBS. Cells were then prepared using the OxiSelect™ Comet Assay Kit (Cell Biolabs, Inc.) following the manufacturer's protocol. The cell suspension was re-centrifuged and resuspended again in ice-cold autoclaved PBS at $1\times10^5$ cells/mL. Cell samples were combined with molten OxiSelect™ Comet Agarose at a 1:10 ratio (v/v), and 75 μL added per well. An overnight lysis in chilled Lysis Buffer at 4° C. was done instead of the 1 h lysis suggested in the manufacturer's protocol. Slides were transferred to chilled Alkaline Solution for 30 min at 4° C., and run on a horizontal electrophoresis apparatus (1V/cm) for 30 min. The slides were then washed three times with deionized water and rinsed with ice-cold 70% ethanol. Slides were allowed to completely dry, and 100 μL Vista Green DNA Dye was added to each well. Twenty comet images from each well were imaged by fluorescence microscopy (Olympus Inverted IX81). The tail moment (Tail DNA %×Length of Tail) was quantified for each cell using Comet Assay IV (Perceptive Instruments).

Results

The effect of AuNP 4 on cytotoxicity and radiation response was tested (FIG. 14) with C4-AuNP as a control. The control C4-AuNP did not cause significant toxicity to either breast cancer cell line MCF-7 or the normal cell controls using the mammary epithelial cell line MCF-10A, showing that gold nanoparticles have low cytotoxicity to cells (17). The minimal reduction of cell viability of C4-AuNP-treated cells after radiation treatment was due to the short time after radiation at which cells were observed: 48 hours post radiation, approximately 20% reduction in cell viability was observed on average.

Figure 14:
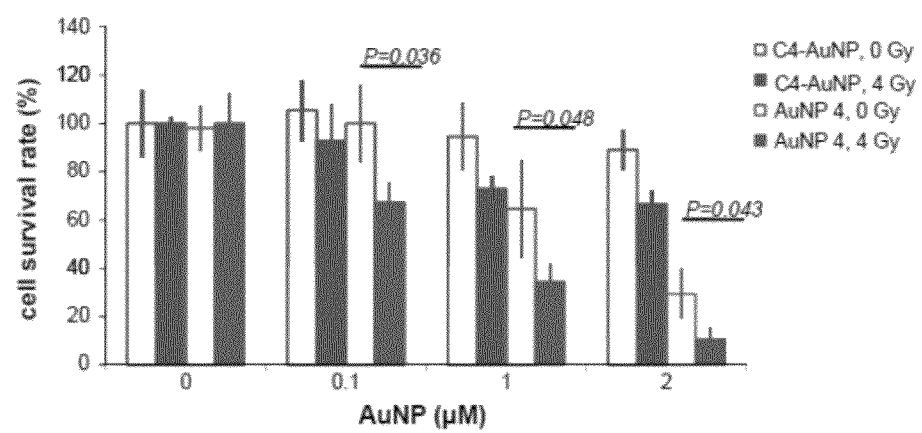
FIG. 14 shows a comparison of cytotoxic and radiation sensitization effects of C4-AuNP and AuNP 4 on MCF-7 cell as assessed by long-term cell survival assay. MCF-7 cells were treated with either C4-AuNP or AuNP 4 at the indicated concentrations for 1 h before irradiation at 4 Gy. After irradiation, cells were incubated for 12 d until colonies formed. Unirradiated MCF-7 cells were also treated with either C4-AuNP or AuNP 4 and incubated for 12 d to determine cell survival rates. Experiments were performed in triplicate, and error bars represent standard deviations.
Figure 15:
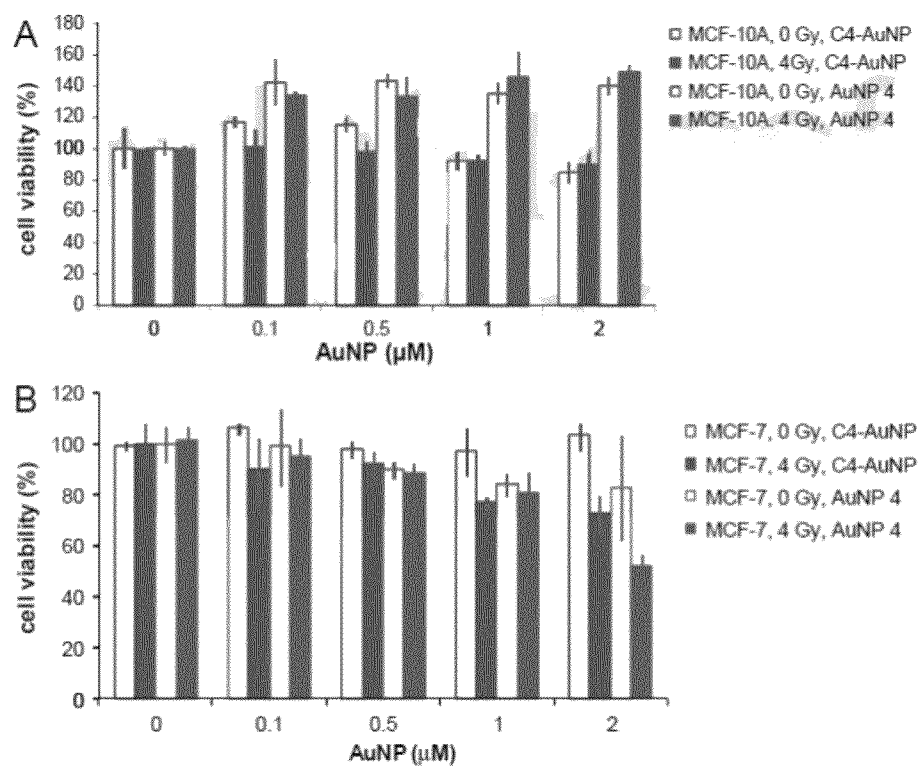
FIG. 15 illustrates the effects of AuNP 4 on cell toxicity and sensitivity to radiation. MCF-10A (A) or MCF-7 (B) cells were plated in 96-well plates one day before nanoparticle treatment and grown to 50% confluency. C4-AuNP or AuNP 4 were added to the cells at the indicated concentrations. One hour after AuNP addition, cells were irradiated (4 Gy) or not and returned to the incubator for an additional 48 h. Shown is cell viability as analyzed by MTS assay.

AuNP 4 reproducibly stimulates the growth of MCF-10 slightly (FIG. 15A), but inhibits the growth of MCF-7 (FIGS. 15B). In addition, it also sensitized MCF-7 to radiation much more significantly than it sensitized MCF-10 cells (FIG. 15). To further confirm the radiation sensitization effect on MCF-7, clonogenic assays were conducted to evaluate long-term cell survival (FIG. 14). AuNP 4 inhibited growth of the cancer cells (MCF-7) and enhanced its sensitivity to radiation.

These findings indicate that AuNP 4 has a role in targeting poly-SUMO chains, and indicate that poly-SUMO chains are also important for proliferation of breast cancer cell MCF-7. Further, these findings are consistent with previous reports that RNF4 and its homologues are important in DNA repair and genome stability (11, 31). The effects of AuNP 4 on proliferation of MCF-7 and MCF-10A cells also suggest that SUMOylation plays a more important role in the growth of the cancer cells than normal cells, which is consistent with previous findings of the key role of SUMOylation in tumorigenesis (32, 33).

Figure 16:
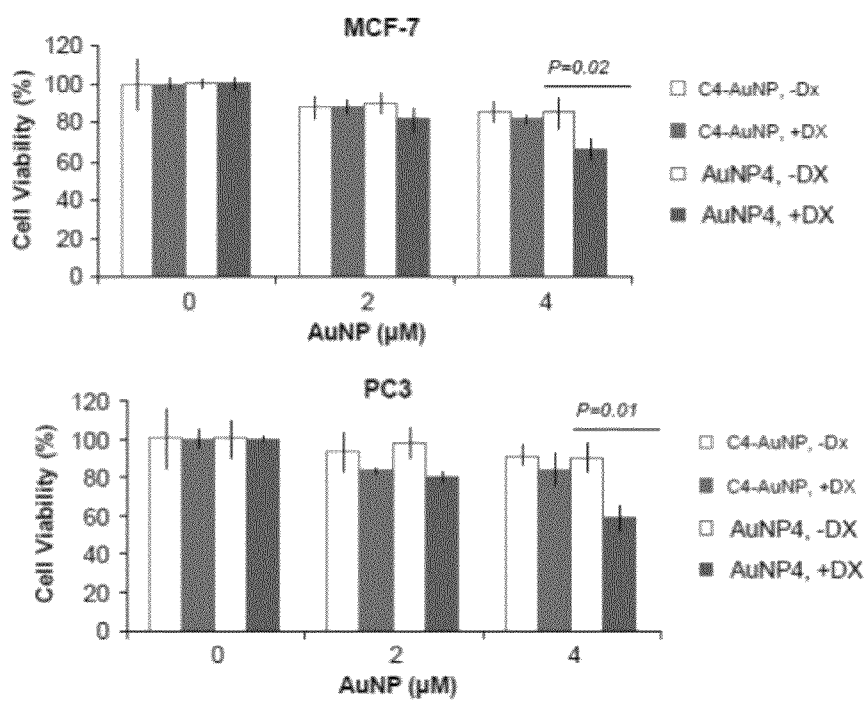
FIG. 16 illustrates the effects of C4-AuNP and AuNP 4 on sensitizing cellular response to doxorubicin (Dx). The breast cancer cell line MCF-7 and prostate cancer cell line PC3 were treated with AuNP 4 or C4-AuNP for 1 h and then exposed to 2 μM doxorubicin for another 48 h. Cell viability was measured by MTS assay.
Figure 17:
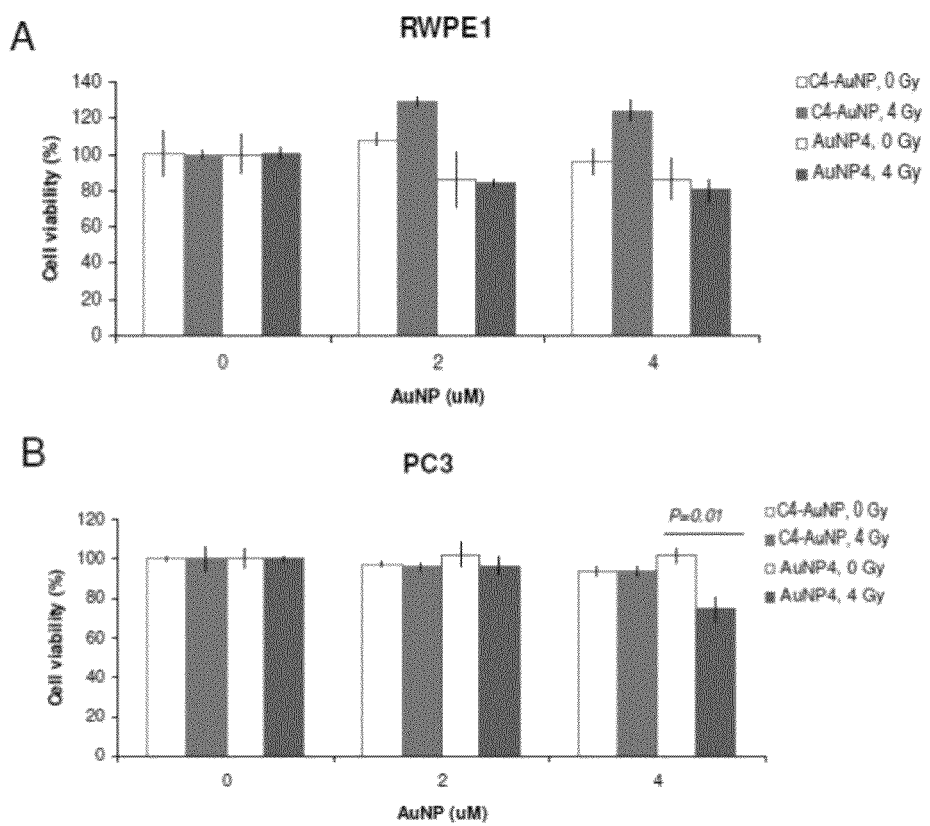
FIG. 17 illustrates the effects of AuNP 4 on cellular toxicity and sensitivity to radiation. Untransformed RWPE-1 prostate epithelial cells (A) or PC3 prostate cancer cells (B) were plated in 96-well plates one day before AuNP treatment and grown to 50% confluency. C4-AuNP or AuNP 4 was added to the wells at the indicated concentrations. After incubation (1 h) with AuNPs, cells were irradiated at 4 Gy or not irradiated and cultured for an additional 48 h. Cell viability was analyzed by MTS assay.

AuNP 4 also sensitized MCF-7 cells to genotoxic stress generated by chemotherapeutic drug doxorubicin (FIG. 16), and sensitized the prostate cancer cell line Pc-3 to radiation and doxorubicin treatment (FIGS. 16 and 17).

Figure 18:
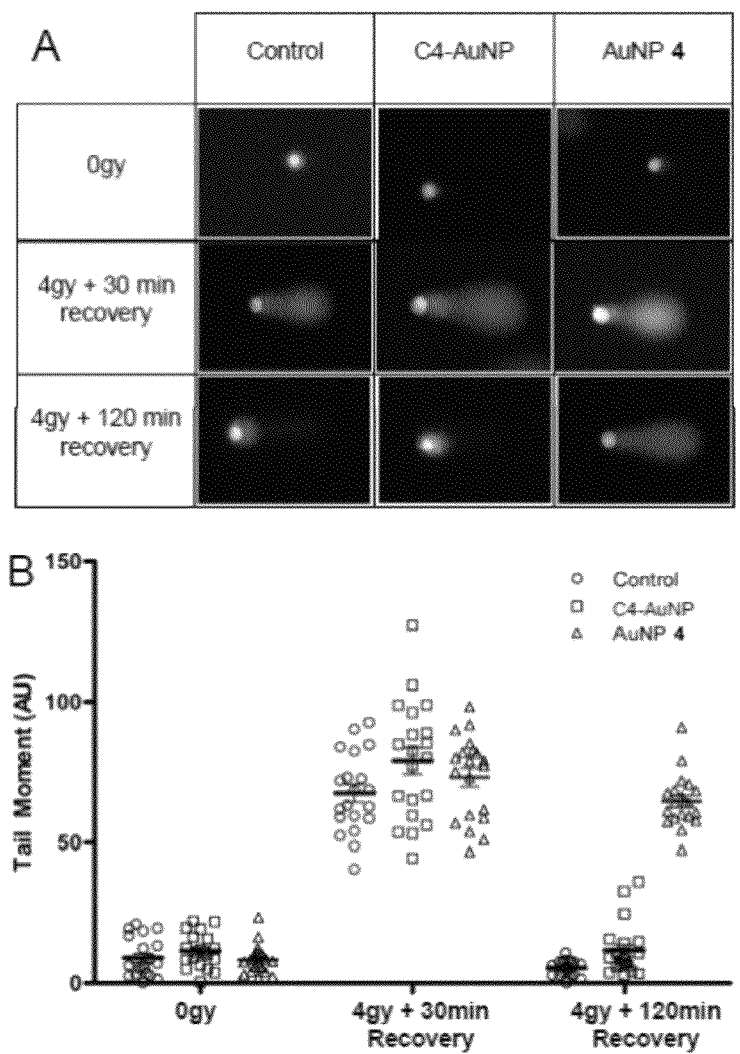
FIG. 18 illustrates detection of DNA damage using comet assays. Comet assays were used to measure the amount of unrepaired DNA damage in untreated cells or cells treated with AuNP 4 or C4-AuNP after γ-irradiation (4 Gy) and recovery for 30 or 120 min. (A) Representative images of the three sets of cells. (B) Tail moments (Tail DNA %×Length of Tail) as quantified for each cell using Comet Assay IV (Perceptive Instruments). Each spot represents a single cell; 20 comet images were measured for each treatment.

To further confirm the inhibitory effect of the SIM peptide on DNA repair, the comet assay was used to measure the amount of DNA damage in cells treated with AuNP 4 or the control C4-AuNP overnight, followed by 4 Gy gamma (γ)-radiation and recovery for 30 or 120 min. In the comet assay, damaged DNA fragments migrate out of the cell nucleus as a streak similar to the tail of a comet, and the quantified tail moments are directly proportional to the amount of DNA damage. Immediately after irradiation, all cells produced comet tails of similar lengths and intensities (FIG. 18). However, after 120 min, the tail moments were significantly larger in cells treated with AuNP 4 than those treated with C4-AuNP or in untreated cells. These data were consistent with the radiation sensitivity data described above, indicating that repair of the damaged DNA was delayed by AuNP 4.

References

The references listed below and those cited in the specification above are hereby incorporated by reference in their entirety as if fully set forth herein.

1. Kerscher, O., Felberbaum, R., & Hochstrasser, M. (2006) Modification of proteins by ubiquitin and ubiquitin-like proteins. *Annu Rev Cell Dev Biol* 22, 159-180.
2. Tatham, M. H., Geoffroy, M. C., Shen, L., Plechanovova, A., Hattersley, N., Jaffray, E. G., Palvimo, J. J., & Hay, R. T. (2008) RNF4 is a poly-SUMO-specific E3 ubiquitin ligase required for arsenic-induced PML degradation. *Nature cell biology* 10, 538-546.
3. Saitoh, H. & Hinchey, J. (2000) Functional heterogeneity of small ubiquitin-related protein modifiers SUMO-1 versus SUMO-2/3. *The Journal of biological chemistry* 275, 6252-6258.
4. Ayaydin, F. & Dasso, M. (2004) Distinct in vivo dynamics of vertebrate SUMO paralogues. *Mol Biol Cell* 15, 5208-5218.
5. Tatham, M. H., Jaffray, E., Vaughan, O. A., Desterro, J. M., Botting, C., Naismith, J. H., & Hay, R. T. (2001) Polymeric chains of SUMO-2 and SUMO-3 are conjugated to protein substrates by SAE1/SAE2 and Ubc9. *The Journal of biological chemistry* 12, 12.
6. Hicke, L., Schubert, H. L., & Hill, C. P. (2005) Ubiquitin-binding domains. *Nature reviews* 6, 610-621.
7. Song, J., Durrin, L. K., Wilkinson, T. A., Krontiris, T. G., & Chen, Y. (2004) Identification of a SUMO-binding motif that recognizes SUMO-modified proteins. *Proceedings of the National Academy of Sciences of the United States of America* 101, 14373-14378.
8. Song, J., Zhang, Z., Hu, W., & Chen, Y. (2005) Small ubiquitin-like modifier (SUMO) recognition of a SUMO binding motif: a reversal of the bound orientation. *The Journal of biological chemistry* 280, 40122-40129.
9. Burgess, R. C., Rahman, S., Lisby, M., Rothstein, R., & Zhao, X. (2007) The SIx5-SIx8 complex affects sumoylation of DNA repair proteins and negatively regulates recombination. *Molecular and cellular biology* 27, 6153-6162.
10. Ii, T., Mullen, J. R., Slagle, C. E., & Brill, S. J. (2007) Stimulation of in vitro sumoylation by SIx5-SIx8: evidence for a functional interaction with the SUMO pathway. *DNA Repair (Amst)* 6, 1679-1691.
11. Prudden, J., Pebernard, S., Raffa, G., Slavin, D. A., Perry, J. J., Tainer, J. A., McGowan, C. H., & Boddy, M. N. (2007) SUMO-targeted ubiquitin ligases in genome stability. *Embo J* 26, 4089-4101.
12. Nagai, S., Dubrana, K., Tsai-Pflugfelder, M., Davidson, M. B., Roberts, T. M., Brown, G. W., Varela, E., Hediger, F., Gasser, S. M., & Krogan, N. J. (2008) Functional targeting of DNA damage to a nuclear pore-associated SUMO-dependent ubiquitin ligase. *Science (New York, N.Y.* 322, 597-602.
13. Cook, C. E., Hochstrasser, M., & Kerscher, O. (2009) The SUMO-targeted ubiquitin ligase subunit SIx5 resides in nuclear foci and at sites of DNA breaks. *Cell Cycle* 8, 1080-1089.
14. Sun, H., Leverson, J. D., & Hunter, T. (2007) Conserved function of RNF4 family proteins in eukaryotes: targeting a ubiquitin ligase to SUMOylated proteins. *Embo J* 26, 4102-4112.

15. Verma, R., et al. (2004) Ubistatins inhibit proteasome-dependent degradation by binding the ubiquitin chain. *Science* (New York, N.Y.306, 117-120.
16. Chithrani, D. B., Jelveh, S., Jalali, F., van Prooijen, M., Allen, C., Bristow, R. G., Hill, R. P., & Jaffray, D. A. Gold nanoparticles as radiation sensitizers in cancer therapy. *Radiation research* 173, 719-728.
17. Butterworth, K. T., Coulter, J. A., Jain, S., Forker, J., McMahon, S. J., Schettino, G., Prise, K. M., Currell, F. J., & Hirst, D. G. Evaluation of cytotoxicity and radiation enhancement using 1.9 nm gold particles: potential application for cancer therapy. *Nanotechnology* 21, 295101.
18. Sekiyama, N., Ikegami, T., Yamane, T., Ikeguchi, M., Uchimura, Y., Baba, D., Ariyoshi, M., Tochio, H., Saitoh, H., & Shirakawa, M. (2008) Structure of the small ubiquitin-like modifier (SUMO)-interacting motif of MBD1-containing chromatin-associated factor 1 bound to SUMO-3. *The Journal of biological chemistry* 283, 35966-35975.
19. Street, A. G. & Mayo, S. L. (1999) Intrinsic beta-sheet propensities result from van der Waals interactions between side chains and the local backbone. *Proceedings of the National Academy of Sciences of the United States of America* 96, 9074-9076.
20. Wang, J., Hu, W., Cai, S., Lee, B., Song, J., & Chen, Y. (2007) The intrinsic affinity between E2 and the Cys domain of E1 in ubiquitin-like modifications. *Mol Cell* 27, 228-237.
21. Miyawaki, A., Miyauchi, M., Takashima, Y., Yamaguchi, H., & Harada, A. (2008) Formation of supramolecular isomers; poly[2] rotaxane and supramolecular assembly. *Chemical communications* (Cambridge, England), 456-458.
22. Boyce R J, Mulqueen G C, & Pattenden G (1995) *Tetrahedron* 51:7321.
23. Brust M, Walker M, Bethell D, Schiffrin D J, & Whyman R (1994) Synthesis of Thiol-derivatised Gold Nanoparticles in a Two-phase Liquid-Liquid System. *Journal of the Chemical Society, Chemical Communications:*801-802.
24. You C-C, De M, Han G, & Rotello VM (2005) Tunable Inhibition and Denaturation of a-Chymotrypsin with Amino Acid-functionalized Gold Nanoparticles. *Journal of the American Chemical Society* 127(37):12873-12881.
25. Hostetler M J, Templeton A C, & Murray R W (1999) (Translated from Eng) *Langmuir* 15(11):3282-3789 (in Eng).
26. Weisshaar S R, et al. (2008) Arsenic trioxide stimulates SUMO-2/3 modification leading to RNF4-dependent proteolytic targeting of PML. (Translated from eng) *FEBS Lett* 582(21-22):3174-3178 (in eng).
27. Thrower J S, Hoffman L, Rechsteiner M, & Pickart C M (2000) Recognition of the polyubiquitin proteolytic signal. (Translated from eng) *The EMBO journal* 19(1):94-102 (in eng).
28. Piotrowski J, et al. (1997) Inhibition of the 26 S proteasome by polyubiquitin chains synthesized to have defined lengths. (Translated from eng) *The Journal of biological chemistry* 272(38):23712-23721 (in eng).
29. Lallemand-Breitenbach V, et al. (2008) Arsenic degrades PML or PML-RARalpha through a SUMO-triggered RNF4/ubiquitin-mediated pathway. (Translated from eng) *Nat Cell Biol* 10(5):547-555 (in eng).
30. Percherancier Y, et al. (2009) Role of SUMO in RNF4-mediated promyelocytic leukemia protein (PML) degradation: sumoylation of PML and phospho-switch control of its SUMO binding domain dissected in living cells. (Translated from eng) *The Journal of biological chemistry* 284(24):16595-16608 (in eng).
31. Kosoy A, Calonge T M, Outwin E A, & O'Connell M J (2007) Fission yeast Rnf4 homologs are required for DNA repair. (Translated from eng) *The Journal of biological chemistry* 282(28):20388-20394 (in eng).
32. Mo Y Y & Moschos S J (2005) Targeting Ubc9 for cancer therapy. (Translated from eng) *Expert Opin Ther Targets* 9(6):1203-1216 (in eng).
33. Zheng Z, et al. (2006) SUMO-3 enhances androgen receptor transcriptional activity through a sumoylation-independent mechanism in prostate cancer cells. (Translated from eng) *The Journal of biological chemistry* 281(7):4002-4012 (in eng).
34. Halgren T A, et al. (2004) Glide: a new approach for rapid, accurate docking and scoring. 2. Enrichment factors in database screening. *J Med Chem* 47(7):1750-1759.
35. Friesner R A, et al. (2004) Glide: a new approach for rapid, accurate docking and scoring. 1. Method and assessment of docking accuracy. *J Med Chem* 47(7):1739-1749.
36. You C C, De M, Han G, & Rotello V M (2005) Tunable inhibition and denaturation of alpha-chymotrypsin with amino acid-functionalized gold nanoparticles. (Translated from eng) *Journal of the American Chemical Society* 127(37):12873-12881 (in eng).
37. Franken N A, Rodermond H M, Stap J, Haveman J, & van Bree C (2006) Clonogenic assay of cells in vitro. (Translated from eng) *Nature protocols* 1(5):2315-2319 (in eng).

What is claimed is:

1. A nanoparticle attached to a plurality of peptides, wherein said peptides are each bound to a different ubiquitin-like protein in a poly-ubl chain; and wherein said peptides form part of a β sheet with each of said ubiquitin-like proteins.
2. The nanoparticle of claim 1, wherein said peptide comprises an amino acid having a branched side chain.
3. The nanoparticle of claim 1, wherein said amino acid is leucine, isoleucine or valine.
4. The nanoparticle of claim 1, wherein said peptide comprises an amino acid having an aromatic side chain.
5. The nanoparticle of claim 4, wherein said peptide comprises a tryptophan, histidine, tyrosine or phenylalanine.
6. The nanoparticle of claim 1, wherein said peptide is bound through hydrophobic interactions to ubiquitin like protein amino acids equivalent to I33 and F31 of Sumo-3.
7. The nanoparticle of claim 1, wherein said peptide is bound through hydrogen bonding interactions to ubiquitin like protein amino acids equivalent to K32 and K34 of Sumo-3.
8. The nanoparticle of claim 1, wherein said peptide consists of two amino acids and a linker attaching said peptide to said nanoparticle.
9. The nanoparticle of claim 8, wherein said nanoparticle is a metal nanoparticle and said linker comprises a sulfur atom bound to said metal nanoparticle.
10. The nanoparticle of claim 9, wherein said linker comprises a phenyl moiety.
11. The nanoparticle of claim 10, wherein said peptide is

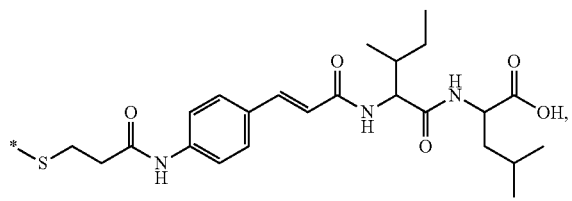 [SMILES: *SCCC(=O)Nc1ccc(/C=C/C(=O)NC(C(=O)NC(CC(C)C)C(=O)O)C(C)CC)cc1]

wherein * represents the point of attachment of the peptide to the metal nanoparticle.

12. The nanoparticle of claim 1, wherein said ubiquitin-like protein is a SUMO protein.

* * * * *